US011763952B2

(12) United States Patent
Haghighi et al.

(10) Patent No.: US 11,763,952 B2
(45) Date of Patent: Sep. 19, 2023

(54) SYSTEMS, METHODS, AND APPARATUSES FOR LEARNING SEMANTICS-ENRICHED REPRESENTATIONS VIA SELF-DISCOVERY, SELF-CLASSIFICATION, AND SELF-RESTORATION IN THE CONTEXT OF MEDICAL IMAGING

(71) Applicant: Arizona Board of Regents on Behalf of Arizona State University, Scottsdale, AZ (US)

(72) Inventors: Fatemeh Haghighi, Tempe, AZ (US); Mohammad Reza Hosseinzadeh Taher, Tempe, AZ (US); Zongwei Zhou, Tempe, AZ (US); Jianming Liang, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 232 days.

(21) Appl. No.: 17/180,575

(22) Filed: Feb. 19, 2021

(65) Prior Publication Data
US 2021/0265043 A1 Aug. 26, 2021

Related U.S. Application Data

(60) Provisional application No. 62/980,069, filed on Feb. 21, 2020.

(51) Int. Cl.
*G06K 9/00* (2022.01)
*G16H 50/70* (2018.01)
(Continued)

(52) U.S. Cl.
CPC ............. *G16H 50/70* (2018.01); *G06F 16/55* (2019.01); *G06F 16/583* (2019.01);
(Continued)

(58) Field of Classification Search
CPC ........ G16H 50/70; G16H 30/20; G16H 30/40; G16H 50/20; G06F 16/55; G06F 16/583;
(Continued)

(56) References Cited

U.S. PATENT DOCUMENTS 10,074,038 B2  9/2018  Hsieh et al.
10,460,440 B2  10/2019  Zhang et al.
(Continued)

OTHER PUBLICATIONS

Alex, V. et al., "Semisupervised learning using denoising autoencoders for brain lesion detection and segmentation," Journal of Medical Imaging, 4(4), 2017, p. 041311.
(Continued)

*Primary Examiner* — Xin Jia
(74) *Attorney, Agent, or Firm* — Elliott, Ostrander & Preston, P.C.

(57) ABSTRACT

Described herein are means for learning semantics-enriched representations via self-discovery, self-classification, and self-restoration in the context of medical imaging. Embodiments include the training of deep models to learn semantically enriched visual representation by self-discovery, self-classification, and self-restoration of the anatomy underneath medical images, resulting in a collection of semantics-enriched pre-trained models, called Semantic Genesis. Other related embodiments are disclosed.

20 Claims, 23 Drawing Sheets

(51) Int. Cl.
  *G16H 30/40* (2018.01)
  *G16H 30/20* (2018.01)
  *G06F 16/55* (2019.01)
  *G06N 3/08* (2023.01)
  *G06F 16/583* (2019.01)
  *G06F 18/28* (2023.01)
  *G06F 18/214* (2023.01)
  *G06V 10/772* (2022.01)
  *G06V 10/82* (2022.01)

(52) U.S. Cl.
  CPC ............ *G06F 18/214* (2023.01); *G06F 18/28* (2023.01); *G06N 3/08* (2013.01); *G06V 10/772* (2022.01); *G06V 10/82* (2022.01); *G16H 30/20* (2018.01); *G16H 30/40* (2018.01)

(58) Field of Classification Search
  CPC ......... G06F 18/214; G06F 18/28; G06N 3/08; G06N 3/045; G06N 3/088; G06V 10/772; G06V 10/82; G06V 2201/031; G06T 2207/20084; G06T 2207/30004; G06T 5/005
  See application file for complete search history.

(56) References Cited

U.S. PATENT DOCUMENTS

| | | | | |
|---|---|---|---|---|
| 11,334,807 | B1* | 5/2022 | O'Shea | G06N 20/00 |
| 2015/0238148 | A1* | 8/2015 | Georgescu | G06T 7/77 600/408 |
| 2016/0174902 | A1* | 6/2016 | Georgescu | G06T 7/0012 600/408 |
| 2019/0108261 | A1* | 4/2019 | Hashemi | G05B 13/00 |
| 2020/0210808 | A1* | 7/2020 | Dong | G06F 18/241 |
| 2021/0342646 | A1 | 11/2021 | Feng et al. | |

OTHER PUBLICATIONS

Aresta, G. et al., "iW-Net: an automatic and minimalistic interactive lung nodule segmentation deep network," Scientific reports, 9(1), 2019, pp. 1-9.
Armato III, S. G. et al., "The lung image database consortium (LIDC) and image database resource initiative (IDRI): a completed reference database of lung nodules on CT scans," Medical physics, 38(2), 2011, pp. 915-931.
Bilic, P. et al., "The liver tumor segmentation benchmark (lits)" 2019, arXiv preprint arXiv:1901.04056.
Caron, M. et al., "Deep clustering for unsupervised learning of visual features," In Proceedings of the European Conference on Computer Vision (ECCV), 2018, pp. 132-149.
Chen, L. et al., "Self-supervised learning for medical image analysis using image context restoration," Medical image analysis, 58, 2019, p. 101539.
Chen, S. et al., "Med3d: Transfer learning for 3d medical image analysis," 2019, arXiv preprint arXiv:1904.00625.
Chen, T. et al., "Self-supervised gans via auxiliary rotation loss," Proceedings of the IEEE Conference on Computer Vision and Pattern Recognition, 2019, pp. 12154-12163.
Deng, J. et al., "Imagenet: A large-scale hierarchical image database," Proceedings of the IEEE Conference on Computer Vision and Pattern Recognition, IEEE, 2009, pp. 248-255.
Deshpande, A. et al., "Learning large-scale automatic image colorization," Proceedings of the IEEE International Conference on Computer Vision, 2015, pp. 567-575.
Ding, Y. et al., "A deep learning model to predict a diagnosis of Alzheimer disease by using 18F-FDG PET of the brain," Radiology, 290(2), 2018, pp. 456-464.
Doersch, C. et al., "Multi-task selfsupervised visual learning," Proceedings of the IEEE International Conference on Computer Vision, 2017, pp. 2051-2060.
Doersch, C. et al., "Unsupervised visual representation learning by context prediction," Proceedings of the IEEE International Conference on Computer Vision, 2015, pp. 1422-1430.
Esteva, A. et al., "Dermatologist-level classification of skin cancer with deep neural networks," Nature, 542(7639), 2107, pp. 115-118.
Feng, Z. et al., "Self-supervised representation learning by rotation feature decoupling," Proceedings of the IEEE Conference on Computer Vision and Pattern Recognition, 2019, pp. 10364-10374.
Gibson, E. et al., "Niftynet: a deep-learning platform for medical imaging." Computer methods and programs in biomedicine, 158, 2018, pp. 113-122.
Gidaris, S. et al., "Unsupervised representation learning by predicting image rotations,"2018, arXiv preprint arXiv:1803.07728.
Goyal, P. et al., Scaling and benchmarking self-supervised visual representation learning, 2019, arXiv preprint arXiv:1905.01235.
Greenspan, H. et al., "Guest editorial deep learning in medical imaging: Overview and future promise of an exciting new technique," IEEE Transactions on Medical Imaging, 35(5), 2016, pp. 1153-1159.
Guan, Q. et al., "Multi-label chest x-ray image classification via category-wise residual attention learning," Pattern Recognition Letters, 130, 2018.
Guendel, S. et al., "Learning to recognize abnormalities in chest x-rays with location-aware dense networks," Iberoamerican Congress on Pattern Recognition, 2018, pp. 757-765. Springer.
He, K. et al., "Deep residual learning for image recognition," Proceedings of the IEEE Conference on Computer Vision and Pattern Recognition, 2016, pp. 770-778.
Huang, G. et al., "Densely connected convolutional networks," Proceedings of the IEEE Conference on Computer Vision and Pattern Recognition, 2017, pp. 4700-4708.
Irvin, J. et al., "Chexpert: A large chest radiograph dataset with uncertainty labels and expert comparison," 2019, arXiv preprint arXiv:1901.07031.
Jamaludin, A. et al., "Self-supervised learning for spinal MRIs," Deep Learning in Medical Image Analysis and Multimodal Learning for Clinical Decision Support: Third International Workshop, DLMIA 2017, and 7th International Workshop, ML-CDS 2017, Held in Conjunction with MICCAI 2017, Québec City, QC, Canada, Sep. 14, Proceedings 3, 2017, pp. 294-302, Springer International Publishing.
Jing, L. et al., "Self-supervised visual feature learning with deep neural networks: A survey," 2019, arXiv preprint arXiv:1902.06162.
Kim, D, et al., " Learning image representations by completing damaged jigsaw puzzles," 2018 IEEE Winter Conference on Applications of Computer Vision (WACV), 2018, pp. 793-802.
Krizhevsky, A. et al., "Imagenet classification with deep convolutional neural networks," Advances in neural information processing systems, 2012, pp. 1097-1105.
Kurmann, T. et al., "Deep multi-label classification in affine subspaces," Medical Image Computing and Computer Assisted Intervention-MICCAI 2019: 22nd International Conference, Shenzhen, China, Oct. 13-17, 2019, Proceedings, Part I 22, pp. 165-173. Springer International Publishing.
Larsson, G. et al., "Colorization as a proxy task for visual understanding," In Proceedings of the IEEE Conference on Computer Vision and Pattern Recognition, 2017, pp. 6874-6883.
Larsson, G. et al., "Learning representations for automatic colorization," Computer Vision-ECCV 2016: 14th European Conference, Amsterdam, The Netherlands, Oct. 11-14, 2016, Proceedings, Part IV 14, pp. 577-593. Springer International Publishing.
Litjens, G. et al., "A survey on deep learning in medical image analysis," Medical image analysis, 42, 2017, pp. 60-88.
Lu, L. et al., "Deep learning and convolutional neural networks for medical image computing: precision medicine, high performance and large-scale datasets," Deep Learning and Convolutional Neural Networks for Medical Image Computing, 2017.
Ma, Y. et al., "Multi-attention network for thoracic disease classification and localization," ICASSP 2019-2019 IEEE International Conference on Acoustics, Speech and Signal Processing (ICASSP), 2019, pp. 1378-1382.
Mahendran, A. et al., "Cross pixel optical-flow similarity for self-supervised learning," Computer Vision-ACCV 2018: 14th Asian

(56) References Cited

OTHER PUBLICATIONS

Conference on Computer Vision, Perth, Australia, Dec. 2-6, 2018, Revised Selected Papers, Part V 14, 2019, pp. 99-116, Springer International Publishing.

Mundhenk, T. N. et al., "improvements to context based self-supervised learning," Proceedings of the IEEE Conference on Computer Vision and Pattern Recognition, 2018, pp. 9339-9348.

Noroozi, M. et al., "Boosting self-supervised learning via knowledge transfer," Proceedings of the IEEE conference on computer vision and pattern recognition, 2018, pp. 9359-9367.

Noroozi, M. et al., "Unsupervised learning of visual representations by solving jigsaw puzzles," Computer Vision—ECCV 2016: 14th European Conference, Amsterdam, The Netherlands, Oct. 11-14, 2016, Proceedings, Part VI, 2016, pp. 69-84, Cham: Springer International Publishing.

Pan, S. J. et al., "A survey on transfer learning," IEEE Transactions on knowledge and data engineering, 22(10), 2010, pp. 1345-1359.

Pathak, D. et al., "Context encoders: Feature learning by inpainting," Proceedings of the IEEE Conference on Computer Vision and Pattern Recognition, 2016, pp. 2536-2544.

Ross, T. et al., "Exploiting the potential of unlabeled endoscopic video data with self-supervised learning," International journal of computer assisted radiology and surgery, 13(6), 2018, pp. 925-933.

Roth, H. R, et al., "A new 2.5 D representation for lymph node detection using random sets of deep convolutional neural network observations," Medical Image Computing and Computer-Assisted Intervention-MICCAI 2014: 17th International Conference, Boston, MA, USA, Sep. 14-18, 2014, Proceedings, Part I 17, 2014, pp. 520-527, Springer International Publishing.

Roth, H. R. et al., "Improving computer-aided detection using convolutional neural networks and random view aggregation," IEEE transactions on medical imaging, 35(5), 2015, pp. 1170-1181.

Sayed, N. et al., "Cross and learn: Cross-modal self-supervision." Pattern Recognition: 40th German Conference, GCPR 2018, Stuttgart, Germany, Oct. 9-12, 2018, Proceedings 40, 2019, pp. 228-243, Springer International Publishing.

Setio, A.A.A. et al., "Pulmonary nodule detection in CT images: false positive reduction using multi-view convolutional networks," IEEE transactions on medical imaging, 35(5), 2016, pp. 1160-1169.

Setio, A.A.A. et al., "Validation, comparison, and combination of algorithms for automatic detection of pulmonary nodules in computed tomography images: the LUNA16 challenge," Medical image analysis, 42, 2017, pp. 1-13.

Shen, D. et al., "Deep learning in medical image analysis," Annual review of biomedical engineering, 19, 2017, pp. 221-248.

Shin H. C. et al., "Deep convolutional neural networks for computer-aided detection: CNN architectures, dataset characteristics and transfer learning," IEEE transactions on medical imaging, 35(5), 2016, pp. 1285-1298.

Spitzer, H. et al., "Improving cytoarchitectonic segmentation of human brain areas with self-supervised siamese networks," Medical Image Computing and Computer Assisted Intervention-MICCAI 2018: 21st International Conference, Granada, Spain, Sep. 16-20, 2018, Proceedings, Part III 11, 2018, pp. 663-671, Springer International Publishing.

Sun, W. et al., "Automatic feature learning using multichannel ROI based on deep structured algorithms for computerized lung cancer diagnosis," Computers in biology and medicine, 89, 2017, pp. 530-539.

Tajbakhsh, N. et al., "Computer-aided detection and visualization of pulmonary embolism using a novel, compact, and discriminative image representation," Medical image analysis, 58, 2019, p. 101541.

Tajbakhsh, N. et al., "Computer-aided pulmonary embolism detection using a novel vessel-aligned multi-planar image representation and convolutional neural networks," Medical Image Computing and Computer-Assisted Intervention—MICCAI 2015: 18th International Conference, Munich, Germany, Oct. 5-9, 2015, Proceedings, Part II 18, 2015, pp. 62-69, Springer International Publishing.

Tajbakhsh, N. et al., "Convolutional neural networks for medical image analysis: Full training or fine tuning?," IEEE transactions on medical imaging. 35(5), 2016, pp. 1299-1312.

Tajbakhsh, N. et al., "Surrogate supervision for medical image analysis: Effective deep learning from limited quantities of labeled data," 2019, arXiv preprint arXiv:1901.08707.

Tang, H. et al., "Nodulenet: Decoupled false positive reduction for pulmonary nodule detection and segmentation," Medical Image Computing and Computer Assisted Intervention—MICCAI 2019: 22nd International Conference, Shenzhen, China, Oct. 13-17, 2019, Proceedings, Part VI 22, 2019, pp. 266-274, Springer International Publishing.

Tang, Y. et al., "Attention-guided curriculum learning for weakly supervised classification and localization of thoracic diseases on chest radiographs," Machine Learning in Medical Imaging: 9th International Workshop, MLMI 2018, Held in Conjunction with MICCAI 2018, Granada, Spain, Sep. 16, 2018, Proceedings 9, 2018, pp. 249-258, Springer International Publishing.

Wang, H. et al., "Comparison of machine learning methods for classifying mediastinal lymph node metastasis of non-small cell lung cancer from 18 F-FDG PET/CT images," EJNMMI research, 7, 2017, pp. 1-11.

Wang, X. et al., "Chestxray8: Hospital-scale chest x-ray database and benchmarks on weakly-supervised classification and localization of common thorax diseases," Proceedings of the IEEE Conference on Computer Vision and Pattern Recognition, 2017, pp. 2097-2106.

Weiss, K. et al., "A survey of transfer learning," Journal of Big Data, 3(1), 2016, pp. 1-40.

Yosinski, J. et al., "How transferable are features in deep neural networks?," Advances in neural information processing systems, 27, 2014, pp. 3320-3328.

Zhang, R. et al., "Colorful image colorization," Computer Vision-ECCV 2016: 14th European Conference, Amsterdam, The Netherlands, Oct. 11-14, 2016, Proceedings, Part III 14, 2016, pp. 649-666, Springer International Publishing.

Zhang, R. et al., "Split-brain autoencoders: Unsupervised learning by cross-channel prediction," Proceedings of the IEEE Conference on Computer Vision and Pattern Recognition, 2017, pp. 1058-1067.

Zhou, Z. et al., "Fine-tuning convolutional neural networks for biomedical image analysis: actively and incrementally," Proceedings of the IEEE Conference on Computer Vision and Pattern Recognition, pp. 7340-7349, 2017.

Zhou, Z. et al., "Models genesis: Generic autodidactic models for 3d medical image analysis," Medical Image Computing and Computer Assisted Intervention—MICCAI 2019: 22nd International Conference, Shenzhen, China, Oct. 13-17, 2019, Proceedings, Part IV 22, 2019, pp. 384-393, Springer International Publishing.

Zhou, Z. et al., "Unet++: A nested u-net architecture for medical image segmentation," Deep Learning in Medical Image Analysis and Multimodal Learning for Clinical Decision Support: 4th International Workshop, DLMIA 2018, and 8th International Workshop, ML-CDS 2018, Held in Conjunction with MICCAI 2018, Granada, Spain, Sep. 20, 2018, Proceedings 4, 2018, pp. 3-11, Springer International Publishing.

\* cited by examiner

180 – Equation 1

FIG. 1B

$$\mathcal{L}_{cls} = -\frac{1}{N}\sum_{b=1}^{N}\sum_{c=1}^{C}\mathcal{Y}_{bc}\log\mathcal{P}_{bc}$$

185 – Equation 2

FIG. 1C

$$\mathcal{L}_{rec} = \frac{1}{N}\sum_{i=1}^{N}\|\mathcal{X}_i - \mathcal{X}'_i\|_2$$

175 - Table 1

FIG. 1D

| Application 176 | 177 Modality | Dataset 178 |
|---|---|---|
| Lung nodule false positive reduction | CT | LUNA-2016 |
| Lung nodule segmentation | CT | LIDC-IDRI |
| Liver segmentation | CT | LiTS-2017 |
| Thorax diseases classification | X-ray | ChestX-Ray14 |

275 - Table 2

| Initialization | 3D nodule false positive reduction | | 3D liver segmentation | | 3D module segmentation | |
|---|---|---|---|---|---|---|
| | AUC(%) | p-value† | IoU(%) | p-value† | IoU(%) | p-value† |
| Random | 94.25±5.07 | 0.0137 | 74.60±4.57 | 1.56e-4 | 74.05±1.97 | 0.0160 |
| Autoencoder | 88.43±10.25 | 0.0063 | 78.16±2.07 | 4.35e-4 | 75.10±0.91 | 0.0086 |
| Inpainting | 91.46±2.97 | 4.59e-5 | 81.36±4.83 | 0.0121 | 75.86±0.26 | 0.0129 |
| Patch shuffling | 91.93±2.32 | 1.39e-5 | 82.82±2.33 | 0.0080 | 75.74±0.51 | 0.0088 |
| Self-restoration | 97.90±0.57 | 0.0062 | 79.52±4.77 | 0.0043 | 77.62±0.64 | 0.4540 |
| Self-classification | 97.41±0.32 | 2.63e-7 | 83.61±2.19 | 0.0224 | 76.23±0.42 | 0.0167 |
| Semantic Genesis 3D | 98.47±0.22 | N/A | 85.60±1.94 | N/A | 77.81±0.68 | N/A |

† p-values are calculated between Semantic Genesis 3D and other counterparts.

FIG. 2B

375 - Table 3

| Disease \ Method Evaluated 376 | Conventional Methodology (Wang, et al.) 377A | Conventional Methodology (Kumann, et al.) 377B | Conventional Methodology (Guendel, et al.) 377C | Conventional Methodology (Guan, et al.) 377D | Disclosed Methodology 380 |
|---|---|---|---|---|---|
| Atelectasis | 0.7003 | 0.7189 | 0.7670 | 0.7810 | 0.7838 |
| Cardiomegaly | 0.8100 | 0.8799 | 0.8830 | 0.8830 | 0.8808 |
| Effusion | 0.7585 | 0.7920 | 0.8280 | 0.8310 | 0.8389 |
| Infiltration | 0.6614 | 0.7205 | 0.7090 | 0.6970 | 0.7062 |
| Mass | 0.6933 | 0.8090 | 0.8210 | 0.8300 | 0.8317 |
| Nodule | 0.6687 | 0.7113 | 0.7580 | 0.7640 | 0.7945 |
| Pneumonia | 0.6580 | 0.7664 | 0.7310 | 0.7250 | 0.7320 |
| Pneumothorax | 0.7993 | 0.8370 | 0.8460 | 0.8660 | 0.8661 |
| Consolidation | 0.7032 | 0.7336 | 0.7450 | 0.7580 | 0.7541 |
| Edema | 0.8052 | 0.8020 | 0.8350 | 0.8530 | 0.8554 |
| Emphysema | 0.8330 | 0.8407 | 0.8950 | 0.9110 | 0.9342 |
| Fibrosis | 0.7859 | 0.8034 | 0.8180 | 0.8260 | 0.8359 |
| PT† | 0.6835 | 0.7570 | 0.7610 | 0.7800 | 0.7991 |
| Hernia | 0.8717 | 0.8722 | 0.8960 | 0.9180 | 0.9021 |
| Average | 0.7451 | 0.7888 | 0.8066 | 0.8159 | 0.8225 |

† Pleural-Thickening

FIG. 3B

395 - Table 4

| Proxy task dataset(s) | IoU (%) | p-value† |
|---|---|---|
| ChestX-ray14 | 71.47±1.40 | 0.0134 |
| LUNA-2016 | 72.20±0.67 | 0.0146 |
| ChestX-ray14 and LUNA-2016 | 73.02±0.56 | N/A |

† p-values are calculated between multiple data sources and others.

FIG. 3C

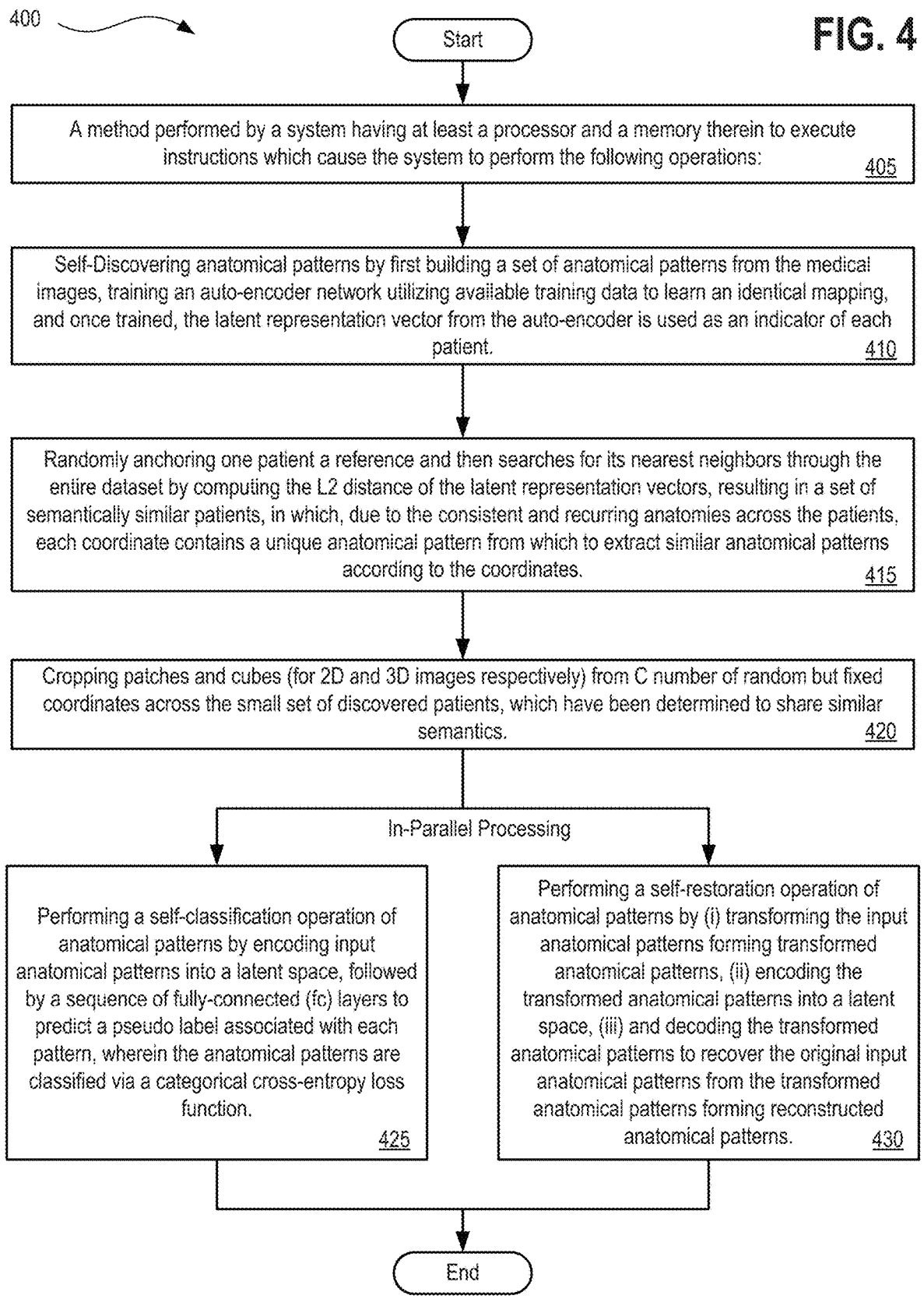

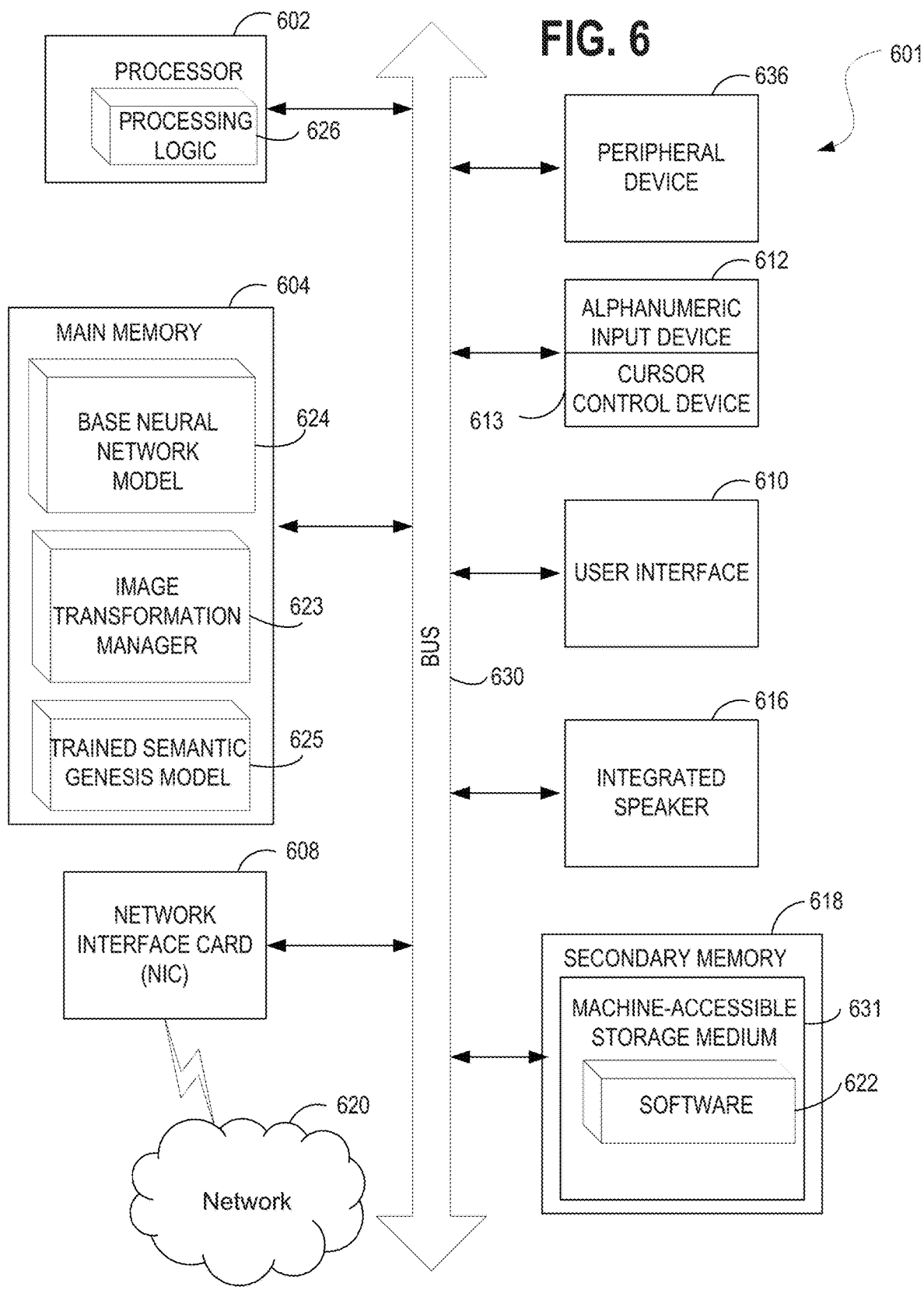

FIG. 7A
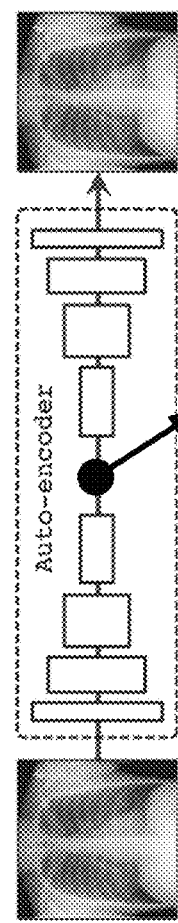
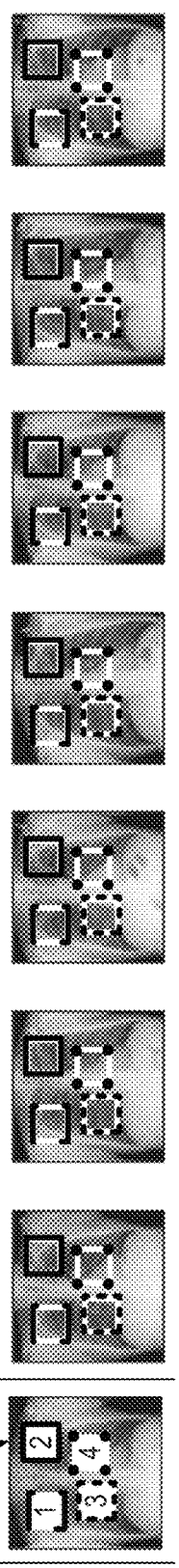
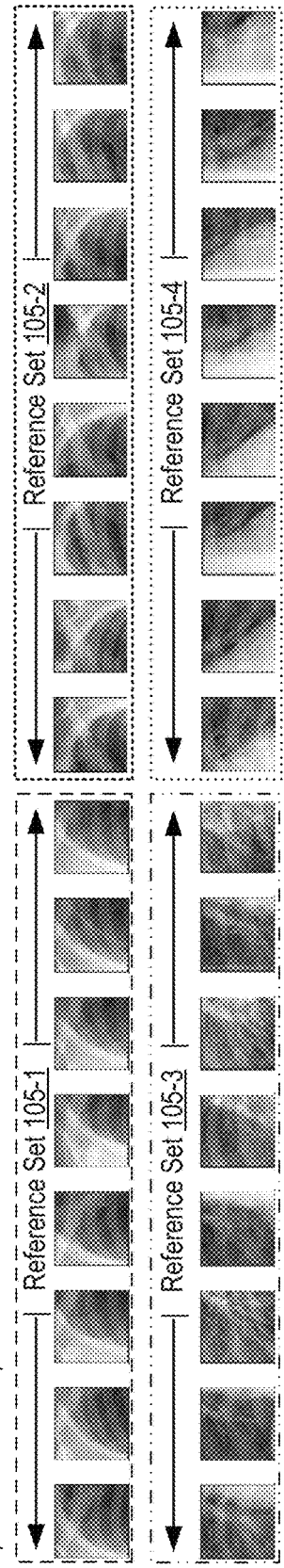

1295 - Table 6

| Initialization | 3D liver segmentation | | 3D module segmentation | |
|---|---|---|---|---|
| | IoU(%) | p-value | IoU(%) | p-value |
| Random | 74.60±4.57 | 1.56e-4 | 74.05±1.97 | 0.0160 |
| NiftyNet | 83.23±1.05 | 0.0021 | 52.98±2.05 | 4.04e-5 |
| MedicalNet | 83.32±0.85 | 0.0025 | 75.68±0.32 | 0.0104 |
| Models Genesis | 79.52±4.77 | 0.0043 | 77.62±0.64 | 0.4540 |
| Semantic Genesis 3D | 85.60±1.94 | N/A | 77.81±0.68 | N/A |

† p-values are calculated between Semantic Genesis 3D and other counterparts.

FIG. 12

SYSTEMS, METHODS, AND APPARATUSES FOR LEARNING SEMANTICS-ENRICHED REPRESENTATIONS VIA SELF-DISCOVERY, SELF-CLASSIFICATION, AND SELF-RESTORATION IN THE CONTEXT OF MEDICAL IMAGING

CLAIM OF PRIORITY

This U.S. Utility patent application is related to, and claims priority to, the U.S. Provisional Patent Application Ser. No. 62/980,069, entitled "SYSTEMS, METHODS, AND APPARATUSES FOR LEARNING SEMANTICS-ENRICHED REPRESENTATIONS VIA SELF-DISCOVERY, SELF-CLASSIFICATION, AND SELF-RESTORATION IN THE CONTEXT OF MEDICAL IMAGING," filed Feb. 21, 2020, the entire contents of which is incorporated herein by reference.

GOVERNMENT RIGHTS AND GOVERNMENT AGENCY SUPPORT NOTICE

This invention was made with government support under R01 HL128785 awarded by the National Institutes of Health. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

Embodiments of the invention relate generally to the field of medical imaging and analysis using convolutional neural networks for the classification and annotation of medical images, and more particularly, to systems, methods, and apparatuses for learning semantics-enriched representations via self-discovery, self-classification, and self-restoration in the context of medical imaging.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to embodiments of the claimed inventions.

Machine learning models have various applications to automatically process inputs and produce outputs considering situational factors and learned information to improve output quality. One area where machine learning models, and neural networks in particular, provide high utility is in the field of processing medical images.

Within the context of machine learning and with regard to deep learning specifically, a Convolutional Neural Network (CNN, or ConvNet) is a class of deep neural networks, very often applied to analyzing visual imagery. Convolutional Neural Networks are regularized versions of multilayer perceptrons. Multilayer perceptrons are fully connected networks, such that each neuron in one layer is connected to all neurons in the next layer, a characteristic which often leads to a problem of overfitting of the data and the need for model regularization. Convolutional Neural Networks also seek to apply model regularization, but with a distinct approach. Specifically, CNNs take advantage of the hierarchical pattern in data and assemble more complex patterns using smaller and simpler patterns. Consequently, on the scale of connectedness and complexity, CNNs are on the lower extreme.

Heretofore, self-supervised learning has been sparsely applied in the field of medical imaging. Nevertheless, there is a massive need to provide automated analysis to medical imaging with a high degree of accuracy so as to improve diagnosis capabilities, control medical costs, and to reduce workload burdens placed upon medical professionals.

Not only is annotating medical images tedious and time-consuming, but it also demands costly, specialty-oriented expertise, which is not easily accessible. To address this challenge, a new framework is newly introduced herein and described in greater detail below, which is configured to train deep models to learn semantically enriched visual representations by self-discovery, self-classification, and self-restoration of the anatomy underneath medical images, resulting in a collection of semantics-enriched pre-trained models, which is referred to herein as "Semantic Genesis."

Problematically, annotating medical imaging is tedious and time-consuming, and demands costly, specialty-oriented knowledge and skills, which are not easily accessible. Furthermore, any misdiagnosis from failure to recognize or correctly identify anatomical structures and abnormalities may result in potentially devastating impacts on patient morbidity and mortality.

Embodiments described herein therefore provide enhanced solutions to improve upon conventionally known image representation and learning techniques by leveraging machine learning models to learn semantically enriched visual representations present within medical imagery through a process of self-discovery, self-classification, and self-restoration of the anatomy underneath medical images, resulting in a collection of semantics-enriched pre-trained models, thus forming the Semantic Genesis of such pre-trained models.

The present state of the art may therefore benefit from the systems, methods, and apparatuses as taught herein having been specially configured for learning semantics-enriched representations via self-discovery, self-classification, and self-restoration in the context of medical imaging as is described herein.

BRIEF DESCRIPTION OF THE DRAWINGS

Embodiments are illustrated by way of example, and not by way of limitation, and can be more fully understood with reference to the following detailed description when considered in connection with the figures in which:

FIG. 1B depicts a categorical cross-entropy loss function at equation 1 used to classify anatomical patterns, according to described embodiments;

FIG. 1C depicts a loss function to compute the L2 distance between an original pattern and a reconstructed pattern which then permits Semantic Genesis to restore the transformed anatomical patterns, according to described embodiments;

FIG. 1D provides Table 1 which summarizes target medical applications adopted by the various experiments:

FIG. 2B provides Table 2 at which shows three distinct target medical applications results averaged by 10 trials (mean±s.d.), according to described embodiments;

FIG. 3B provides Table 3 which shows that the Semantic Genesis 2D model outperforms the state-of-the-art methods on the NIH ChestX-ray14 dataset, yielding the best average AUC score over all 14 diseases as well as the highest individual AUC scores for 9 diseases;

FIG. 3C provides Table 4 which shows the results of an ablation study on a target lung nodule segmentation task suggesting that when pre-training Semantic Genesis, combining data sources offers better target performance than a single data source;

FIG. 4 depicts a flow diagram illustrating a method for learning semantics-enriched representations via self-discovery, self-classification, and self-restoration in the context of medical imaging, in accordance with disclosed embodiments;

FIG. 6 illustrates a diagrammatic representation of a machine in the exemplary form of a computer system, in accordance with one embodiment;

FIGS. 7A and 7B show how Semantic Genesis is dramatically different from Models Genesis and other prior known solutions in both methodology and performance;

FIG. 12 provides Table 6 which compares Semantic Genesis with publicly available pre-trained 3D models.

DETAILED DESCRIPTION

Described herein are methods and systems for learning semantics-enriched representations via self-discovery, self-classification, and self-restoration in the context of medical imaging.

Medical images are naturally associated with rich semantics about the human anatomy, reflected in abundant recurring anatomical patterns, offering unique potential to foster deep semantic representation learning and yield semantically more powerful models for different medical applications. But how exactly such strong yet free semantics embedded in medical images can be harnessed for self-supervised learning remains largely unexplored.

Described herein are means by which to train deep models to learn semantically enriched visual representations through self-discovery, self-classification, and self-restoration of the human anatomy underlying or embedded within medical images, resulting in a collection of semantics-enriched pre-trained models, referred to herein as Semantic Genesis.

Such specially trained and configured Semantic Genesis models have been evaluated using four medical imaging datasets from LUNA-2016, LIDC-IDRI, LiTS-2017, and ChestX-ray14, covering multiple imaging modalities in both 2D and 3D. These evaluations, as will be described in greater detail below, demonstrate that the Semantic Genesis model surpasses publicly available pre-trained models in 3D as well as the de facto ImageNet-based transfer learning in 2D. This improved performance is attributed to the novel self-supervised learning framework, which encourages deep models to learn compelling semantic representations from abundant anatomical patterns resulted from consistent anatomies embedded in medical images.

Figure 1A:
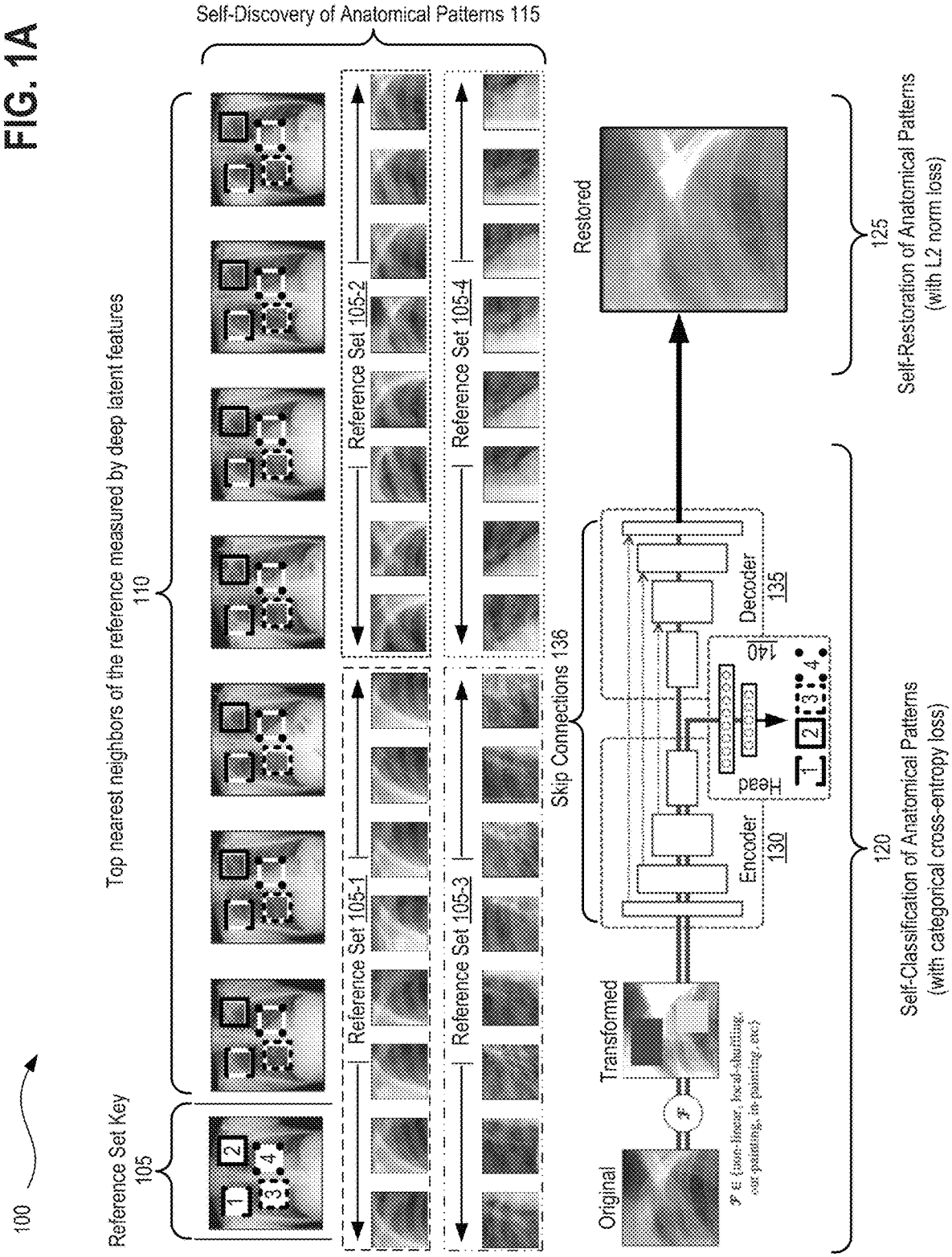
FIG. 1A depicts the self-discovery of anatomical patterns in which the top nearest neighbors of a reference image are measured by deep latent features, which then leads to the self-classification of anatomical patterns with categorical cross-entropy loss, followed by the self-restoration of anatomical patterns with L2 norm loss, in accordance with described embodiments.

FIG. 1A depicts the self-discovery of anatomical patterns in which the top nearest neighbors of a reference image are measured by deep latent features (see element 110), which then leads to the self-classification of anatomical patterns with categorical cross-entropy loss (see element 120), followed by the self-restoration of anatomical patterns with L2 norm loss (see element 120).

The self-supervised learning framework depicted here consists of (a) processing for self-discovery at element 115, (b) processing for self-classification at element 120, and (c) processing for self-restoration of anatomical patterns at element 125, resulting in semantics-enriched pre-trained models—Semantic Genesis—an encoder-decoder structure (see encoder 130 and decoder 135) with skip connections 136 in-between and a classification head 140 at the end of the encoder 130. Given a random reference patient, similar patients are identified based on deep latent features, anatomical patterns are then cropped from random yet fixed coordinates, and pseudo labels are assigned to the cropped anatomical patterns according to their coordinates.

For simplicity and clarity, the concept is depicted here with only four coordinates in X-ray images (refer to the reference set key at element 105 showing coordinates 1, 2, 3, and 4), however, this is only an example and the quantity of coordinates may vary. The input to the model is a transformed anatomical pattern crop, and the model is trained to classify the pseudo label and to recover the original crop as is discussed below, utilizing the cropped anatomical patterns as set forth at Reference sets 105-1, 105-2, 105-3, and 105-4, which correspond to the coordinates 1, 2, 3, and 4 as indicated by the reference set key at element 105. In such a way, the model aims to acquire semantics-enriched representation, producing more powerful application-specific target models.

Self-supervised learning methods aim to learn general image features from unlabeled data. Naturally, a crucial question in self-supervised learning is how to "extract" proper supervision signals from the unlabeled data directly. In large part, self-supervised learning approaches involve predicting some hidden properties of the data, such as grayscale image colorization, image jigsaw puzzle, image rotation, etc. However, most prior known methods were derived in the context of natural images, without considering the unique properties that medical imaging has to offer.

With respect to medical imaging specifically, it is required to follow protocols for defined clinical purposes, generating images of similar anatomies across patients and yielding recurrent anatomical patterns across images (Refer to FIG. 1A, element 115). These recurring patterns are associated with rich semantic knowledge about the human body, thereby offering great potential to foster deep semantic representation learning and produce more powerful models for various medical applications. However, it remains an unanswered question: How to exploit the deep semantics associated with recurrent anatomical patterns embedded in medical images to enrich representation learning? To answer this question, a novel self-supervised learning method is described herein, which enables the capture of semantics-enriched representation from unlabeled medical image data, resulting in a set of powerful pre-trained models. The resulting pre-trained models, are referred to herein as "Semantic Genesis" models because they have been created by utilizing a portion of the source code available from Models Genesis, an open science initiative that invites collaborations and contributions from researchers worldwide.

As illustrated in FIG. 1A, Semantic Genesis represents a significant extension and improvement over Models Genesis by augmenting with self-discovery and self-classification of the anatomy underneath medical images. Compared with Models Genesis, the classification branch in Semantic Genesis shares an encoder with the existing restoration branch and only requires a small computational overhead, and yet, significantly enriches representation learning with semantics from abundant anatomical patterns by self-discovery and self-classification. This is most evident when considering the empirical results set forth below which demonstrate that: (1) learning semantics enriches the existing self-supervised learning approaches on par (see FIG. 2A below); (2) Semantic Genesis offer performance superior to other self-supervised learning counterparts (see Table 2 at FIG. 2B), including Models Genesis; and (3) Semantic Genesis surpasses the fully supervised ImageNet models under the same 2D condition (see FIG. 3A below). This result is significant and unprecedented since no self-supervised learning method has, thus far, outperformed ImageNet models across diseases, organs, and modalities.

This performance is attributed to the semantics derived from the consistent and recurrent anatomical patterns, that not only can be automatically discovered from medical images but also can serve as strong yet free supervision signals for deep models to learn more semantically enriched representation automatically via self-supervision.

Practice of the described embodiments and use of the new Semantic Genesis models in the manner taught herein, therefore provide the following at least the following benefits over existing self-supervised learning approaches: (i) the new Semantic Genesis models provide a collection of generic semantics-enriched pre-trained models in both 2D and 3D effectively across diseases and organs; an entirely new and novel efficient training scheme, encouraging models to learn semantically enriched features from the consistent and recurrent anatomy embedded in medical images by self-discovery 115, self-classification 120, and self-restoration 125; a scalable, self-supervised learning framework, showing that learning semantics from anatomical patterns enrich existing self-supervised learning approaches on par; provided statistical analysis, demonstrating that the Semantic Genesis 3D model as taught herein is superior to not only any publicly available pre-trained models created from either self-supervision or fully supervision in 3D, but also superior to state-of-the-art fully supervised ImageNet models in 2D through four distinct medical applications; and the state of the art is advanced for thorax disease classification in ChestXray14, achieving the best average Area Under the Curve (AUC) as well as the best AUC on nine individual diseases over previous methods.

With the success of deep neural networks, transfer learning has become integral to many applications, especially medical imaging. This immense popularity of transfer learning is attributed to the learned visual representation offering convergence speedups and performance gains for most target tasks, in particular, with limited annotated data.

Supervised representation learning: Pre-training models on a large scale natural image dataset (such as ImageNet) and then fine-tuning the model on different medical imaging tasks has seen the most practical adoption in the medical image analysis. To classify the common thoracic diseases from ChestX-ray14 dataset, nearly all the leading methods follow the paradigm of "fine-tuning ImageNet models" by adopting different architectures, such as ResNet and DenseNet, along with their pre-trained weights. Other representative medical applications include identifying skin cancer from dermatologist level photographs, offering early detection of Alzheimer's Disease, and performing effective detection of pulmonary embolisms.

Despite the remarkable transferability of ImageNet models in multiple medical applications, 2D ImageNet pre-trained models offer little benefits to 3D medical imaging tasks in the most prominent medical modalities (e.g. CT and MRI). To fit this paradigm, 3D imaging tasks have to be reformulated and solved in 2D or 2.5D, losing rich 3D anatomical information and inevitably compromising the performance. This limitation has led to the development of the model zoo in NiftyNet. However, such models were trained with small datasets for specific applications (e.g., brain parcellation and organ segmentation), and never intended as source models for transfer learning. NiftyNet models offer limited benefits to their target medical applications via transfer learning. Previously known techniques utilizing pre-trained 3D residual networks operate by jointly segmenting the labeled objects tagged with a collection of eight medical datasets, resulting in MedicalNet for 3D transfer learning.

Notably, each and every above-mentioned pre-trained model approach requires massive, high-quality annotated datasets. However, the reality is that perfectly-sized and systematically-labeled datasets are rarely available by which to pre-train a deep model in medical imaging. Moreover, even where such data sets exist, both the data and the annotations are expensive to acquire. These limitations are overcome via the self-supervised learning techniques described herein, which allow models to learn visual representations from abundant unlabeled medical image data with zero human annotation effort required.

Self-supervised representation learning: Aiming at learning visual representation from unlabeled data, self-supervised learning research has recently experienced a surge in computer vision, but it is a relatively new trend in medical imaging, including predicting the distance and 3D coordinates of two patches randomly sampled from the same brain, identifying whether two scans belong to the same person, and predicting the level of vertebral bodies. Regardless, prior known techniques simply do not learn representations absolutely from "self-supervision" because they demand auxiliary information and specialized data collection such as paired and registered images.

By utilizing only the original pixel and voxel (e.g., volumetric pixel) information shipped with data, several self-supervised learning schemes have been conducted for different medical applications including: (i) colorization as proxy task, wherein color colonoscopy images are converted to gray-scale and then recovered using a conditional Generative Adversarial Network (GAN); pre-training a stack of de-noising auto-encoders, in which the self-supervision is created by mapping the patches with the injected noise to the original patches; image restoration as proxy task, in which small regions are shuffled within images and then models are permitted to learn to restore the original ones; and individualized self-supervised schemes for a set of target tasks.

However, the above described and previously known self-supervised learning schemes, both in computer vision and medical imaging, are developed individually for specific target tasks, and therefore, the generalizability and robustness of the learned visual representations have yet been examined across multiple target tasks.

Other approaches utilizing generic autodidactic models for 3D medical imaging, which learn common visual representation that is transferable and generalizable across diseases, organs and modalities, seek to overcome the scalability issue associated with multiple tasks. However, these generic models learn from unlabeled data in different perspectives, and as such, the consistent and recurrent anatomy embedded in medical images has not been fully exploited. By explicitly employing this strong yet free semantic supervision signals into a self-supervised learning framework as is done via the described methodologies, the Semantic Genesis models are demonstrated, under the same 2D condition, to outperform ImageNet models, as verified by multiple target tasks.

Method: With reference again to FIG. 1A above, a self-supervised learning framework is presented which enables the training of a specially configured Semantic Genesis model from scratch utilizing only unlabeled medical images.

The Semantic Genesis model is straightforward, utilizing an encoder-decoder structure (elements 130 and 135) with skip connections 136 in between and a classification head 140 at the end of the encoder 130. The objective of the model is to learn different sets of semantics-enriched representation from multiple perspectives. In so doing, the described framework brings about three important components: 1) self-discovery of anatomical patterns 115 from similar patients; 2) self-classification of the anatomical patterns 120; and 3) self-restoration of the anatomical patterns 125 from the transformed patterns.

Specifically, once the self-discovered anatomical pattern set is built, the classification and restoration branches are jointly trained together in the Semantic Genesis model.

Each of the operations are described below, in detail, along with their learning perspectives, as follows:

Operational phase 1—Self-discovery of anatomical patterns: First, a set of anatomical patterns is built from the medical images, as illustrated in FIG. 1A, element 115. To extract deep features of each patient scan, an auto-encoder network is trained utilizing available training data, which learns an identical mapping from scan to itself. Once trained, the latent representation vector from the auto-encoder is used as an indicator of each patient. One patient is then randomly anchored as a reference and processing then searches for its nearest neighbors (refer to element 110) through the entire dataset by computing the L2 distance of the latent representation vectors, resulting in a set of semantically similar patients.

As shown in FIG. 1A, element 115, due to the consistent and recurring anatomies across these patients, that is, each coordinate contains a unique anatomical pattern, it is then feasible to extract similar anatomical patterns according to the coordinates. Processing therefore crops patches and cubes (for 2D and 3D images respectively) from C number of random but fixed coordinates across this small set of discovered patients, which have been determined to share similar semantics.

Processing then computes similarities at the patient-level, rather than the pattern-level, so as to ensure the balance between the diversity and consistency within the anatomical patterns. Lastly, pseudo labels are assigned to the cropped patches and cubes based on their coordinates, resulting in a newly formed dataset, in which each case is associated with one of the C classes. Because the coordinates are randomly selected in the reference patient, the anatomical patterns in most of the classes may not be meaningful for human doctors. However, they are still associated with rich local semantics of the human body and thus useful to the Semantic Genesis model. For example, as shown in FIG. 1A, element 115, pseudo labels are defined randomly in the reference patient (refer to the reference set key 105 at top-left most portion of the diagram), but as seen, they carry local information including anterior ribs 2-4 as represented by extracted reference set 105-1, anterior ribs 1-3 as represented by extracted reference set 105-2, right pulmonary artery as represented by extracted reference set 105-3, and left ventricle (LV), as represented by extracted reference set 105-4. Most importantly, by repeating above self-discovery process, enormous anatomical patterns associated with their pseudo labels are automatically generated for representation learning in the subsequent processing stages.

FIG. 1B depicts a categorical cross-entropy loss function at equation 1 (element 180), used to classify anatomical patterns, according to described embodiments.

Operational phase 2—Self-classification of anatomical patterns: After self-discovery of a set of anatomical patterns, the representation learning is formulated as a simple C-way multi-class classification task. The goal is to encourage models learning from the recurrent anatomical patterns across patient images and therefore to foster a deep semantically enriched representation. As illustrated in FIG. 1A, element 120, the classification branch in the model encodes the input anatomical pattern into a latent space, followed by a sequence of fully-connected (fc) layers, and then predicts the pseudo label associated with the pattern. To classify the anatomical patterns, a categorical cross-entropy loss function is utilized, which is defined below via equation 1 as set forth at FIG. 1B, element 180, where N denotes the batch size; where C denotes the number of classes; where Y and P represent the ground truth (one-hot pseudo label vector) and the prediction, respectively.

FIG. 1C depicts a loss function at equation 2 (element 185) used to compute the L2 distance between an original pattern and a reconstructed pattern which then permits Semantic Genesis to restore the transformed anatomical patterns, according to described embodiments.

Operational phase 3—Self-restoration of anatomical patterns: The objective of self-restoration process is for the model to learn different sets of visual representations by recovering original anatomical patterns from the transformed ones. Four transformations are therefore utilized, including (i) non-linear, (ii) local-shuffling, (iii) out-painting, and (iv) in-painting. Specifically, each anatomical pattern undergoes at most three of above transformations resulting in a transformed pattern (refer to the visualizations of the transformed patterns 805-840 as set forth at FIG. 8, below). As shown in FIG. 1A, element 125, the restoration branch in the model encodes the input transformed anatomical pattern into a latent space and decodes back to the original resolution, with an aim to recover the original anatomical pattern from the transformed one. To let Semantic Genesis restore the transformed anatomical patterns, the L2 distance between the original pattern and the reconstructed pattern is then computed as a loss function, which is defined below via equation 2 as set forth at FIG. 1C, element 185, where N denotes the batch size, and where X and X' represent the ground truth (original anatomical pattern) and the reconstructed prediction, respectively.

Formally, during training, a multi-task loss is defined for each transformed anatomical pattern as $\mathcal{L} = \lambda_{cls}\mathcal{L}_{cls} + \lambda_{rec}\mathcal{L}_{rec}$, where $\lambda_{cls}$ and $\lambda_{rec}$ regulate the weights of classification and reconstruction losses, respectively. The definition of $L_{cls}$ allows the model to learn more semantically enriched representation. The definition $L_{rec}$ of encourages the model learning from multiple perspectives by restoring original images from varying image deformations.

Once trained, the encoder (see element 130 of FIG. 1A) alone may be fine-tuned for target classification tasks; while the encoder and decoder together (130 and 135) may be fine-tuned for target segmentation tasks. This is in contrast to most popular pre-trained models, for example ImageNet models, which can only provide a pre-trained encoder network.

FIG. 1D provides Table 1 at element 175, which summarizes target medical applications adopted by the various experiments.

Experiments—Pre-training Semantic Genesis: With respect to Semantic Genesis 3D, a self-supervised model was pre-trained from 623 CT scans using LUNA-2016 (refer to the dataset column at element 178). While 888 scans were provided by LUNA-2016, the full set was not used for the training of Semantic Genesis so as to avoid test-image leaks between proxy and target tasks. In so doing, the rest of the images were confidently used solely for testing Semantic Genesis as well as the target models. The Semantic Genesis model was trained from only unlabeled images, involving no annotation shipped with the dataset.

To extract the training cubes, processing first randomly selected one patient scan as the reference and then further processing sought to identify the top 200 most similar cases according to the deep features computed from the pre-trained auto-encoder.

Further processing then cropped cubes from these 201 cases, with one individual reference image being randomly selected as a single patient reference scan and with an additional 200 most similar cases being sought out and attained as similar cases according to the deep features computed from the pre-trained auto-encoder. Cubes are them cropped from the 201 cases at C=44 random but fixed coordinates across the 201 patients to cover the lung area. For each random coordinate, three multi-resolution cubes were extracted, thus resulting in 26,532 total cubes. Finally, all the cubes were re-scaled into 64×64×32. Further processing then assigned 44 pseudo labels to cubes based on their coordinates. To pre-train Semantic Genesis 3D, original cubes and their pseudo labels were used as ground truths of the restoration and classification branches, respectively.

Experiments—Semantic Genesis 2D: The Semantic Genesis 2D is self-supervised pre-trained from a combination of two datasets, using 2D CT slices in axial view and X-ray images, from LUNA-2016 and ChestX-ray14, respectively. Processing extracted anatomical patterns at 49 and 44 random coordinates from the X-ray images and CT slices, respectively, and therefore obtained C=93 unique classes in total. All the cropped anatomical patterns are resized into 224×224 and assigned one of the 93 pseudo labels. As seen, Semantic Genesis 2D is pre-trained from mixed data sources, covering CT and X-ray.

Transfer learning from Semantic Genesis: Once Semantic Genesis is pre-trained, the learned representation is evaluated by fine-tuning it within four medical imaging applications including 3D and 2D image classification and segmentation tasks (as summarized by Table 1 at FIG. 1D), across diseases and organs.

Lung nodule false positive reduction: The dataset is provided by LUNA-2016 consists of 888 low-dose lung CTs with slice thickness less than 2.5 mm (refer to the application column at element 176 of Table 1, top row). Patients are randomly assigned into a training set (445 cases), a validation set (178 cases), and a test set (265 cases). The dataset offers the annotations for a set of 5,510,166 candidate locations for the false positive reduction task, in which true positives are labeled as "1" and false positives are labeled as "0". Performance was evaluated via an Area Under the Curve (AUC) score on classifying true positives and false positives.

Lung nodule segmentation: The dataset is provided by the Lung Image Database Consortium image collection (LIDC-IDRI) and consists of 1,018 cases collected by seven academic centers and eight medical imaging companies (refer to the application column at element 176 of Table 1, second row). The cases were split into training (510), validation (100), and test (408) sets. Each case is a 3D CT scan and the nodules have been marked as volumetric binary masks (refer to the modality column at element 177 of Table 1). The volumes were re-sampled to 1-1-1 spacing and then processed to extract a 64×64×32 crop around each nodule. These 3D crops were then used for model training and evaluation. An Intersection over Union (IoU) score was utilized to evaluate performance.

Liver segmentation: The dataset is provided by MICCAI 2017 LiTS Challenge and consists of 200 CT scans, which we split into training (100 patients), validation (15 patients), and test (15 patients) subsets (refer to the application column at element 176 of Table 1, third row). The ground truth segmentation provides two different labels: liver and lesion. Only liver was considered a positive class and others deemed to be a negative class. Segmentation performance was then evaluated using an Intersection over Union (IoU) score.

Thorax diseases classification: ChestX-ray14 is a hospital-scale chest X-ray dataset, which consists of 112,120 frontal-view X-ray images taken from 30,805 patients where 51,708 images have at least one of the 14 thorax diseases (refer to the application column at element 176 of Table 1, last row). ChestX-ray14 provides an official patient-wise split for training (86,524 images) and test (25,596 images) sets with 14 disease labels (each image can have multi-labels). The official splitting of the dataset was used in multi-label chest X-ray classifications to diagnose 14 thorax abnormalities on the ChestX-ray14 dataset. An average AUC score over 14 diseases is reported as well as the AUC score for each individual disease.

Baselines and implementation: Since most self-supervised learning methods are initially proposed and implemented in 2D, the two most representative ones were extended into their 3D version for a fair comparison. In addition, publicly available pre-trained models for 3D transfer learning in medical imaging were examined, including NiftyNet, MedicalNet, and Models Genesis, as well as ImageNet models, the most influential weights initialization in 2D target tasks. The 3D U-Net architecture was used in 3D applications and the U-Net architecture was used in 2D applications. Both of them were modified by appending fully connected (fc) layers to the end of the encoders. In proxy tasks, we set $\lambda rec=1$ and $\lambda cls=0.01$. Adam with a learning rate of 0.001 was used for optimization. Processing first trained the classification branch for 20 epochs, then jointly trained the entire model for both classification and restoration tasks (refer to FIG. 8 for additional image deformations details).

For CT target applications, the capability of both 3D volume-based solutions and 2D slice-based solutions were investigated, where the 2D representation was obtained by extracting axial slices from volumetric datasets. For all applications, each method was run 10 times on the target task, then reporting the average, standard deviation, and further statistical analysis based on an independent two-sample t-test.

Figure 2A:
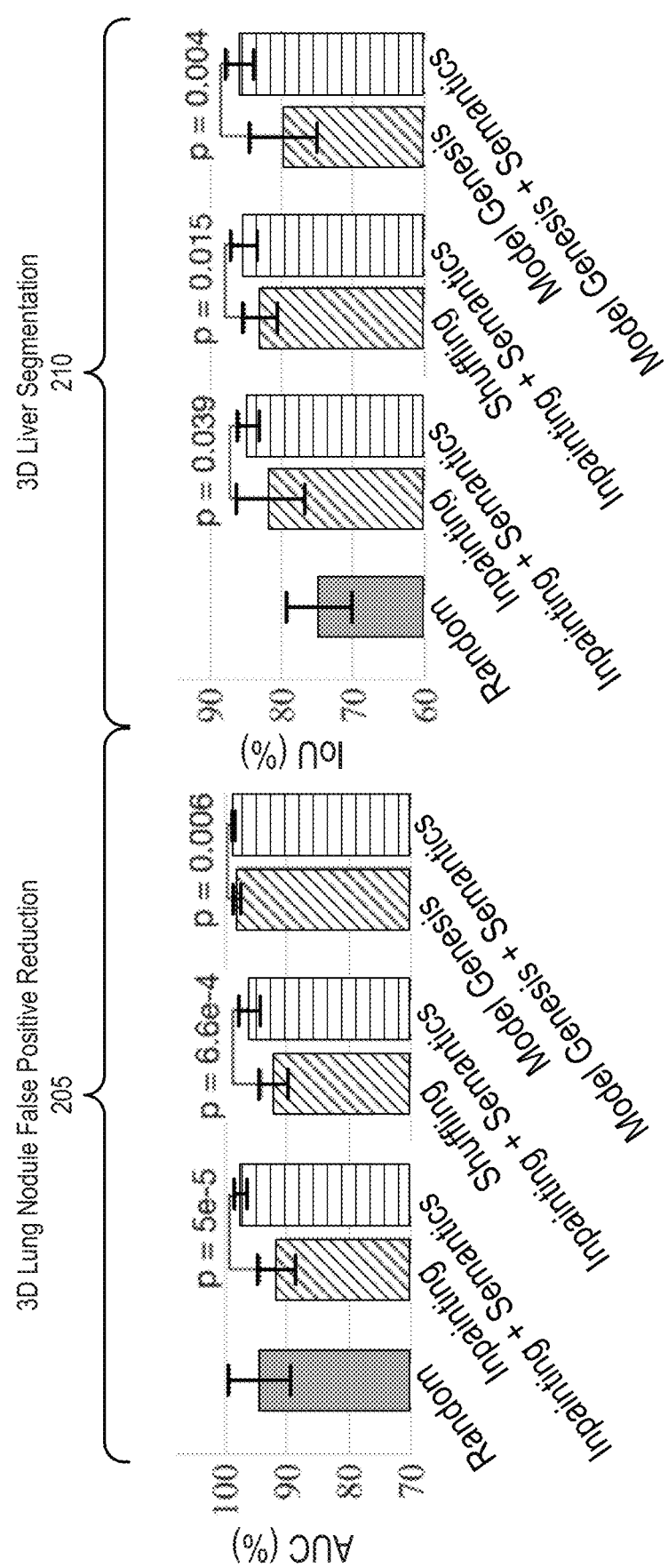
FIG. 2A depicts results both with and without semantics-enriched representations in the existing self-supervised learning approaches contrast a substantial performance difference on target 3D classification and segmentation tasks, according to described embodiments.

FIG. 2A depicts results both with and without semantics-enriched representations in the existing self-supervised learning approaches contrast a substantial ($p<0.05$) performance difference on target 3D classification and segmentation tasks.

Results—Learning semantics enriches the existing self-supervised learning approaches on par: Image restoration serves as one of the most generic and scalable self-supervised methods in 3D medical imaging, managing to generate powerful target models effective across disease, organs, and most importantly, modalities. To inherit such an advantage, processing utilized the three most common image restoration based learning schemes were adopted, i.e. image in-painting, patch-shuffling, and Models Genesis, pursuant to which further processing then enhanced semantics into these learning schemes. Since all of the above image restoration tasks utilize the encoder-decoder architecture with skip connections in between, additional fully-connected (fc) layers are appended to the end of encoder to enable models to learn the image representation simultaneously from both pattern classification and pattern restoration tasks. The described methodology leverages 2D implemented self-supervised learning methods and extends those into 3D implemented self-supervised learning methods.

The effectiveness of semantics-enriched pre-training against their individual self-supervised learning counterparts in two distinct 3D medical target tasks, covering classification and segmentation was evaluated.

As shown in FIG. 2A, simply incorporating the anatomical patterns with representation learning, the semantics-enriched models consistently outperform each and every previously known self-supervised learning method. Specifically, in lung nodule false positive reduction as represented by the table on the left at element 205, the semantics-enriched representation learning achieves performance gains by 5%, 3%, and 1% compared with in-painting, patch-shuffling, and Models Genesis, respectively; and in liver segmentation as represented by the table on the right at element 210, the performance gains yield by 3%, 2%, and 6% once combined with semantically enriched representation learning. The self-supervised learning scheme described herein, which operates by autonomously discovering and classifying anatomical patterns, learns a unique and complementary visual representation in comparison with that learned from image restoration task. Through such a combination, learning from multiple perspectives is enforced for the models, especially from the consistent and recurring anatomical structure, resulting in a more generic and robust image representation.

FIG. 2B provides Table 2 at element 275, which shows three distinct target medical applications results averaged by 10 trials (mean±s.d.) suggesting that fine-tuning 3D models from the Semantic Genesis significantly ($p<0.05$) outperforms those from alternative self-supervised learning approaches and those learning from scratch. The results also demonstrate that a unification of self-discovery, self-classification, and self-restoration of semantics in Semantic Genesis yields a set of generic, robust representations that can be transferred to various target tasks.

Semantic Genesis 3D outperforms publicly available pre-trained models: The Semantic Genesis 3D model was compared with the competitive publicly available pre-trained models and transferred to three distinct 3D medical target applications. Statistical analysis results in Table 2 as depicted at FIG. 2A suggest three major results. First, compared with learning 3D models from scratch, fine-tuning models from Semantic Genesis offers performance gains by at least 3%, and meanwhile, yields more stable performances in all three applications. Second, fine-tuning models from Semantic Genesis achieves significantly higher performances than those fine-tuning from other self-supervised approaches in all three 3D distinct medical applications, specifically: 3D lung nodule false-positive reduction as represented at element 277, lung nodule segmentation as represented at element 278, and liver segmentation as represented at element 279. In particular, Semantic Genesis surpasses Models Genesis, the state-of-the-art 3D pre-trained models created by image restoration based self-supervised learning. Finally, even though Semantic Genesis learns its representation without using any human annotation, it was nevertheless examined with 3D models pre-trained from full supervision, in particular, via MedicalNet and NiftyNet, and included in the detailed comparison (refer to Table 5 as set forth at FIG. 12, element 1295).

Simply stated, Semantic Genesis (AUC=98.47%±0.22%) outperforms MedicalNet (AUC=95.45%) on lung nodule false positive reduction. Conversely, Semantic Genesis benefits explicitly from the deep semantic feature enriched by self-discovering and self-classifying anatomical patterns embedded in medical images, and thus contrasts with any other existing 3D models pre-trained by either self-supervision or full supervision.

Figure 3A:
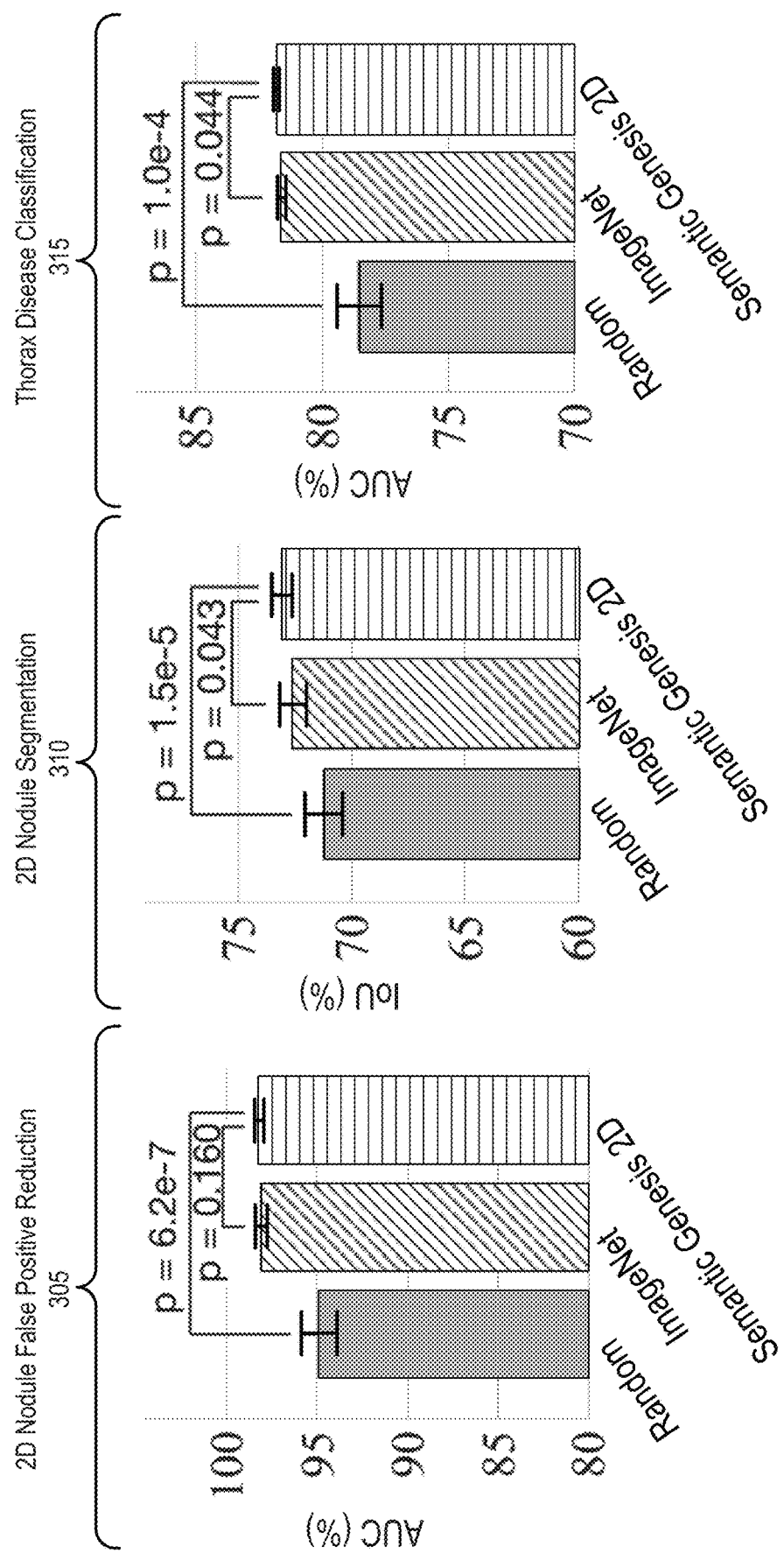
FIG. 3A provides comparison charts showing that Semantic Genesis 2D significantly outperforms ImageNet-based transfer learning in 2 out of 3 target applications, according to described embodiments.

FIG. 3A provides comparison charts showing that Semantic Genesis 2D significantly ($p<0.05$) outperforms ImageNet-based transfer learning in 2 out of 3 target applications, with the same training schedule and the same DenseNet-121 backbone.

Semantic Genesis 2D surpasses state-of-the-art fully supervised ImageNet models: Transfer learning from ImageNet models has become a de facto standard across many different medical applications. Despite the marked domain gap between natural images and medical images, no self-supervised learning approach thus far has outperformed fully supervised pre-trained ImageNet models in 2D medical imaging because ImageNet demands more than 14 million manually labeled images, which carry strong human intelligent semantics.

The Semantic Genesis 2D model was evaluated against ImageNet models for three target tasks, covering classification and segmentation in CT and X-ray. As evidenced by the statistical analyses as presented in FIG. 3, the Semantic Genesis 2D model significantly surpasses fully supervised ImageNet models in 2 out of 3 target applications, i.e. 2D lung nodule segmentation 310 and thorax disease classification 315. Further still, the Semantic Genesis 2D model offers performance equivalent to ImageNet models in lung nodule false positive reduction 305. The performance improvement from the Semantic Genesis to ImageNet-based transfer learning was noticeable and unprecedented because no 2D self-supervised learning approach has thus far been reported to outperform ImageNet models across multiple applications, with zero expert annotation effort.

Utilizing the self-supervised learning framework as taught herein, the anatomical patterns are automatically learned by models directly from image data through self-discovery, self-classification, and self-restoration without any human annotation effort or involvement whatsoever.

FIG. 3B provides Table 3 at element 375, which shows that the Semantic Genesis 2D model outperforms the state-of-the-art methods on the NIH ChestX-ray14 dataset, yielding the best average AUC score over all 14 diseases as well as the highest individual AUC scores for 9 diseases.

Semantic Genesis 2D holds the top solution in ChestX-Ray14: The Semantic Genesis 2D model was evaluated using the official splitting of ChestX-ray14. Table 3 presents the performance of the Semantic Genesis 2D model against previously known state-of-the-art records. As discussed above, the Semantic Genesis 2D model, empowered by semantics-enriched representation, holds the highest classification performance in 9 out of 14 diseases for the methods evaluated (see left-most column 376) and attains top solution with the best average AUC score over 14 diseases (see right-most column 380, specifically the average of 0.8225 in bold). Notably, amongst all of the depicted competitors, and without using any additional data, the Semantic Genesis 2D model, as disclosed (see column 380) outperforms all previously known methodologies, including conventional methodologies 377A, 377B, 377C, and 377D to which the disclosed methodology 380 was directly compared. Prior approaches include utilization of category-wise residual attention learning which employs the correlations among pathologies, holding the previous best performance reported in this dataset. However, the Semantic Genesis 2D model described herein outperforms even that best known approach by at least 2%. It is therefore contemplated that the Semantic Genesis 2D model described herein will become a complementary tool for use in conjunction with the prior best known methods so as to improve patient diagnosis overall.

FIG. 3C provides Table 4 at element 395, which shows the results of an ablation study on a target lung nodule segmentation task suggesting that when pre-training Semantic Genesis, combining data sources offers better target performance than a single data source.

Self-classification and self-restoration lead to complementary representation: The Semantic Genesis 3D model described herein benefits from at least two sources, specifically: pattern classification and pattern restoration. A further ablation study was therefore conducted to investigate the effect of each isolated training scheme (refer to Table 2 at FIG. 2B). The combined training scheme (via Semantic Genesis 3D) consistently and significantly provided performance higher and more stable compared with each of isolated training schemes (self-restoration and self-classification). Moreover, self-restoration and self-classification reveal alternatively better performances in three target applications. These complementary results are attributed to the different visual representations captured from each isolated pre-training scheme, leading to different behaviors in different target applications. These complementary representations, in turn, confirm the importance of the unification of self-classification and self-restoration as utilized by the Semantic Genesis model described herein as well as its significance for the medical imaging field.

Impact of multiple medical data sources on representation learning: The Semantic Genesis model, with zero annotation effort, significantly surpasses state-of-the-art ImageNet-based transfer learning in 2 out of 3 target applications as shown via the charts provided at FIG. 3A. However, the performance improvement is relatively small, suggesting that semantics of anatomy from the large-scale medical data may not be fully exploited. The impact of multiple medical data sources on representation learning was therefore investigated.

The Semantic Genesis model was pre-trained on LUNA-2016, ChestX-ray14, and their combination so as to report the target task performance of lung nodule segmentation. Table 4 shows that representation learning from the mixed data results in a notable performance improvement in the target task, confirming the importance of dataset scale and diversity in self-supervised learning. More diverse and massive medical data sources will therefore advance the capabilities of the described Semantic Genesis model even further, performing effectively across datasets, disease, and, most importantly, modalities.

The self-supervised learning framework as described herein therefore not only allows deep models to learn common visual representation from image data directly, but also leverages semantics-enriched representation from the consistent and recurrent anatomical patterns, one of a broad set of unique properties that medical imaging has to offer. To confirm this advantage, the pre-trained Semantic Genesis was validated on LUNA-2016, LIDC-IDRI, LiTS-2017, and ChestX-ray14, covering classification and segmentation target tasks across diseases and organs. Demonstrated results show that: (1) Semantic Genesis 3D is superior to publicly available models in 3D pre-trained by either self-supervision or even full supervision, and (2) Semantic Genesis 2D surpasses ImageNet-based transfer learning, leading to the state-of-the-art in thorax disease classification. These outstanding results are attributable to the compelling deep semantics learned from abundant anatomical patterns resulting from consistent anatomies naturally embedded in medical images.

FIG. 4 depicts a flow diagram illustrating a method 400 for learning semantics-enriched representations via self-discovery, self-classification, and self-restoration in the context of medical imaging, in accordance with disclosed embodiments. Method 400 may be performed by processing logic that may include hardware (e.g., circuitry, dedicated logic, programmable logic, microcode, etc.), software (e.g., instructions run on a processing device) to perform various operations such as designing, defining, retrieving, parsing, persisting, exposing, loading, executing, operating, receiving, generating, storing, maintaining, creating, returning, presenting, interfacing, communicating, transmitting, querying, processing, providing, determining, triggering, displaying, updating, sending, etc., in pursuance of the systems and methods as described herein. For example, the system 501 (see FIG. 5) and the machine 601 (see FIG. 6) and the other supporting systems and components as described herein may implement the described methodologies. Some of the blocks and/or operations listed below are optional in accordance with certain embodiments. The numbering of the blocks presented is for the sake of clarity and is not intended to prescribe an order of operations in which the various blocks must occur.

With reference to the method 400 depicted at FIG. 4 beginning at block 405, there is a method performed by a system having at least a processor and a memory therein to execute instructions which cause the system to perform the following operations:

At block 410, processing logic performs self-discovery of anatomical patterns by first building a set of anatomical patterns from the medical images, training an auto-encoder network utilizing available training data to learn an identical mapping, and once trained, the latent representation vector from the auto-encoder is used as an indicator of each patient.

At block 415, processing logic randomly anchors one patient a reference and then searches for its nearest neighbors through the entire dataset by computing the L2 distance of the latent representation vectors, resulting in a set of semantically similar patients, in which, due to the consistent and recurring anatomies across the patients, each coordinate contains a unique anatomical pattern from which to extract similar anatomical patterns according to the coordinates.

At block 420, processing logic crops patches and cubes (for 2D and 3D images respectively) from C number of random but fixed coordinates across the small set of discovered patients, which have been determined to share similar semantics.

Method 400 next advances into a parallel processing phase in which both blocks 425 and 430 are performed simultaneously, concurrently, or at least partially in parallel, in accordance with described embodiments.

In particular, at block 425, processing logic performs a self-classification operation of anatomical patterns by encoding input anatomical patterns into a latent space, followed by a sequence of fully-connected (fc) layers to predict a pseudo label associated with each pattern, wherein the anatomical patterns are classified via a categorical cross-entropy loss function and concurrent processing simultaneously executes block 430, performing a self-restoration operation of anatomical patterns by (i) transforming the input anatomical patterns forming transformed anatomical patterns, (ii) encoding the transformed anatomical patterns into a latent space, (iii) and decoding the transformed anatomical patterns to recover the original input anatomical patterns from the transformed anatomical patterns forming reconstructed anatomical patterns.

Simultaneous processing then concludes and method 400 ends.

According to another embodiment of method 400, simultaneous processing executes both the self-classification operation and the self-restoration operation in parallel.

According to another embodiment, method 400 further includes: training a Semantic Genesis model by having the Semantic Genesis model simultaneously classify and restore the transformed anatomical patterns.

According to another embodiment of method 400, performing the method works with both 2D and 3D input images.

According to another embodiment, method 400 further includes: computing an L2 distance between the original input anatomical patterns and the reconstructed anatomical patterns as a loss function.

According to another embodiment of method 400, transforming the input anatomical patterns forming transformed anatomical patterns includes applying one or more transformation functions selected from the group including: (i) a non-linear transformation function, (ii) a local-shuffling transformation function, (iii) a out-painting transformation function, and (iv) a in-painting transformation function.

According to another embodiment of method 400, the patient scans within the dataset are not manually annotated.

According to a particular embodiment, there is a non-transitory computer readable storage medium having instructions stored thereupon that, when executed by a system having at least a processor and a memory therein, the instructions cause the system to perform operations including: performing a self-discovery operation of anatomical patterns by (i) extracting deep features from each of a plurality of patient scans within a dataset, (ii) training an auto-encoder network utilizing training data, and (iii) selecting a random patient scan from the dataset of input images 1039 (e.g., medical images) in which the selected random patient scan becomes a reference image and identifying a set of semantically similar patients to the reference image within the dataset; performing a self-classification operation of anatomical patterns by encoding input anatomical patterns into a latent space, followed by a sequence of fully-connected (fc) layers to predict a pseudo label associated with each pattern, in which the anatomical patterns are classified via a categorical cross-entropy loss function; and performing a self-restoration operation of anatomical patterns by (i) transforming the input anatomical patterns forming transformed anatomical patterns which is managed by transformation functions of the image transformation manager 550, (ii) encoding the transformed anatomical patterns into a latent space, (iii) and decoding the transformed anatomical patterns to recover the original input anatomical patterns from the transformed anatomical patterns forming reconstructed anatomical patterns 1043.

Figure 5:
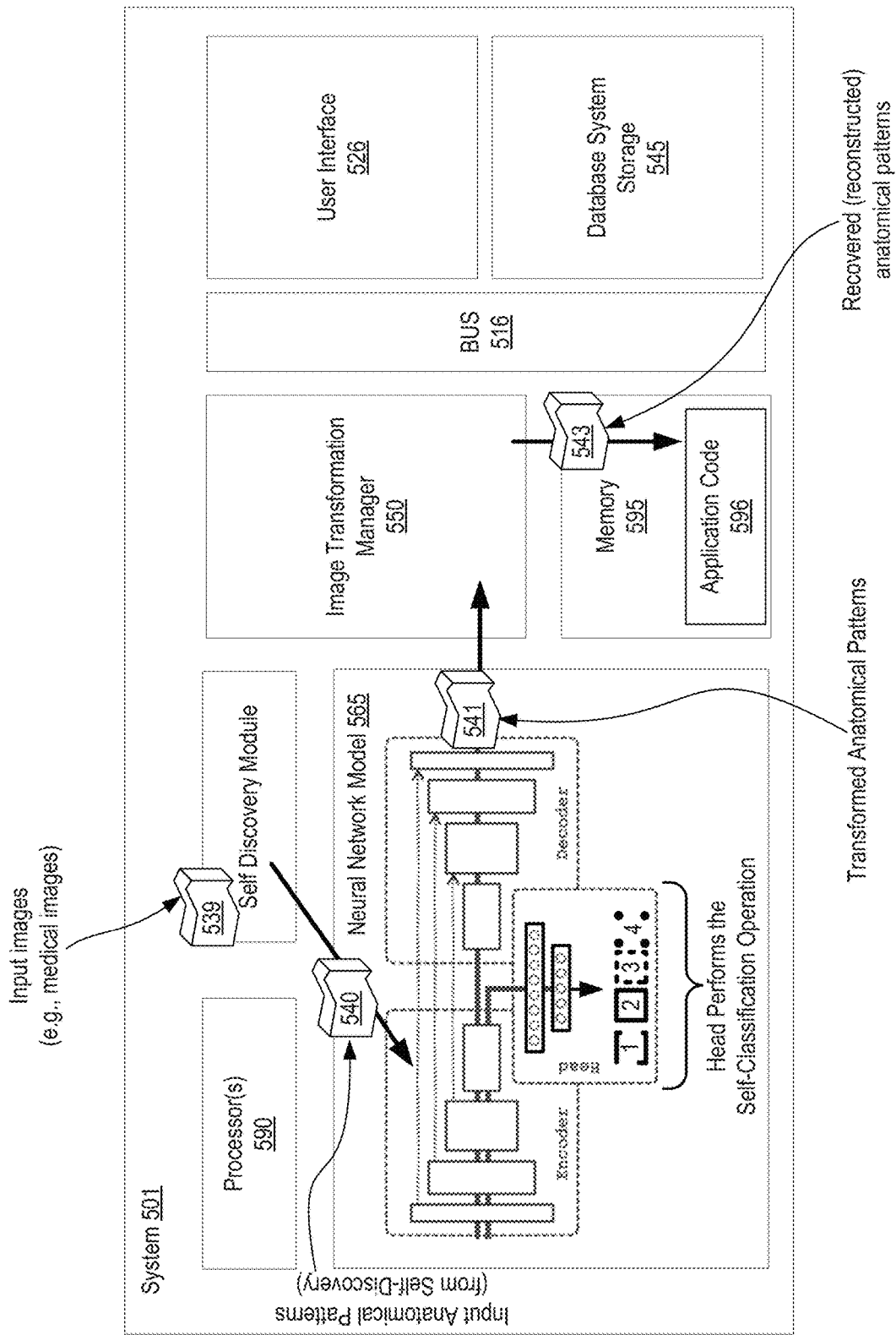
FIG. 5 shows a diagrammatic representation of a system within which embodiments may operate, be installed, integrated, or configured in accordance with certain embodiments.

FIG. 5 shows a diagrammatic representation of a system 501 within which embodiments may operate, be installed, integrated, or configured. In accordance with one embodiment, there is a system 501 having at least a processor 590 and a memory 595 therein to execute implementing application code 596. Such a system 501 may communicatively interface with and cooperatively execute with the benefit of remote systems, such as a user device sending instructions and data, a user device to receive segmented image 543 output from the model output manager 585 of the system, or systems within a networked or within a client-server environment, etc.

According to the depicted embodiment, the system 501, includes the processor 590 and the memory 595 to execute instructions at the system 501 and wherein the system is specially configured to: execute instructions via the processor for performing a self-discovery operation of anatomical patterns by (i) extracting deep features from each of a plurality of patient scans within a dataset, (ii) training an auto-encoder network utilizing training data, and (iii) selecting a random patient scan from the dataset of input images 539 (e.g., medical images) in which the selected random patient scan becomes a reference image and identifying a set of semantically similar patients to the reference image within the dataset. The self-discovery module generates input anatomical patterns 540 for the Neural Network Model 565. The system 501 performs a self-classification operation of anatomical patterns by encoding input anatomical patterns into a latent space, followed by a sequence of fully-connected (fc) layers to predict a pseudo label associated with each pattern, in which the anatomical patterns are classified via a categorical cross-entropy loss function; and performing a self-restoration operation of anatomical patterns by (i) transforming the input anatomical patterns 540 forming transformed anatomical patterns 541 which is managed by transformation functions of the image transformation manager 550, (ii) encoding the transformed anatomical patterns into a latent space, (iii) and decoding the transformed anatomical patterns to recover the original input anatomical patterns from the transformed anatomical patterns forming reconstructed anatomical patterns 543.

The model output manager 585 may further transmit output back to a user device or other requestor, for example, via the user interface 526, including sending a disease classification 543 output to a user device or other requestor, or such information may alternatively be stored within the database system storage 545 of the system 501.

According to another embodiment of the system 501, a user interface 526 communicably interfaces with a user client device remote from the system and communicatively interfaces with the system via a public Internet.

Bus 516 interfaces the various components of the system 501 amongst each other, with any other peripheral(s) of the system 501, and with external components such as external network elements, other machines, client devices, cloud computing services, etc. Communications may further include communicating with external devices via a network interface over a LAN, WAN, or the public Internet.

FIG. 6 illustrates a diagrammatic representation of a machine 601 in the exemplary form of a computer system, in accordance with one embodiment, within which a set of instructions, for causing the machine/computer system 601 to perform any one or more of the methodologies discussed herein, may be executed. In alternative embodiments, the machine may be connected (e.g., networked) to other machines in a Local Area Network (LAN), an intranet, an extranet, or the public Internet. The machine may operate in the capacity of a server or a client machine in a client-server network environment, as a peer machine in a peer-to-peer (or distributed) network environment, as a server or series of servers within an on-demand service environment. Certain embodiments of the machine may be in the form of a personal computer (PC), a tablet PC, a set-top box (STB), a Personal Digital Assistant (PDA), a cellular telephone, a web appliance, a server, a network router, switch or bridge, computing system, or any machine capable of executing a set of instructions (sequential or otherwise) that specify and mandate the specifically configured actions to be taken by that machine pursuant to stored instructions. Further, while only a single machine is illustrated, the term "machine" shall also be taken to include any collection of machines (e.g., computers) that individually or jointly execute a set (or multiple sets) of instructions to perform any one or more of the methodologies discussed herein.

The exemplary computer system 601 includes a processor 602, a main memory 604 (e.g., read-only memory (ROM), flash memory, dynamic random access memory (DRAM) such as synchronous DRAM (SDRAM) or Rambus DRAM (RDRAM), etc., static memory such as flash memory, static random access memory (SRAM), volatile but high-data rate RAM, etc.), and a secondary memory 618 (e.g., a persistent storage device including hard disk drives and a persistent database and/or a multi-tenant database implementation), which communicate with each other via a bus 630. Main memory 604 includes a first neural network model 624 for performing initial self-discovery and self-classification operations and an image transformation manager 623 by which to re-construct original input anatomical images after transformation operations and a trained semantic genesis model 625 having been trained by letting the semantic genesis model perform self-restoration of the transformed anatomical patterns, which collectively are utilized to implement the self-discovery, self-classification, and self-restoration operations for learning semantics-enriched representations in the context of medical imaging in support of the methodologies and techniques described herein. Main memory 604 and its sub-elements are further operable in conjunction with processing logic 626 and processor 602 to perform the methodologies discussed herein.

Processor 602 represents one or more specialized and specifically configured processing devices such as a microprocessor, central processing unit, or the like. More particularly, the processor 602 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 602 may also be one or more special-purpose processing devices such as an application-specific integrated circuit (ASIC), a field programmable gate array (FPGA), a digital signal processor (DSP), network processor, or the like. Processor 602 is configured to execute the processing logic 626 for performing the operations and functionality which is discussed herein.

The computer system 601 may further include a network interface card 608. The computer system 601 also may include a user interface 610 (such as a video display unit, a liquid crystal display, etc.), an alphanumeric input device 612 (e.g., a keyboard), a cursor control device 613 (e.g., a mouse), and a signal generation device 616 (e.g., an integrated speaker). The computer system 601 may further include peripheral device 636 (e.g., wireless or wired communication devices, memory devices, storage devices, audio processing devices, video processing devices, etc.).

The secondary memory 618 may include a non-transitory machine-readable storage medium or a non-transitory computer readable storage medium or a non-transitory machine-accessible storage medium 631 on which is stored one or more sets of instructions (e.g., software 622) embodying any one or more of the methodologies or functions described herein. The software 622 may also reside, completely or at least partially, within the main memory 604 and/or within the processor 602 during execution thereof by the computer system 601, the main memory 604 and the processor 602 also constituting machine-readable storage media. The software 622 may further be transmitted or received over a network 620 via the network interface card 608.

Figure 7B:
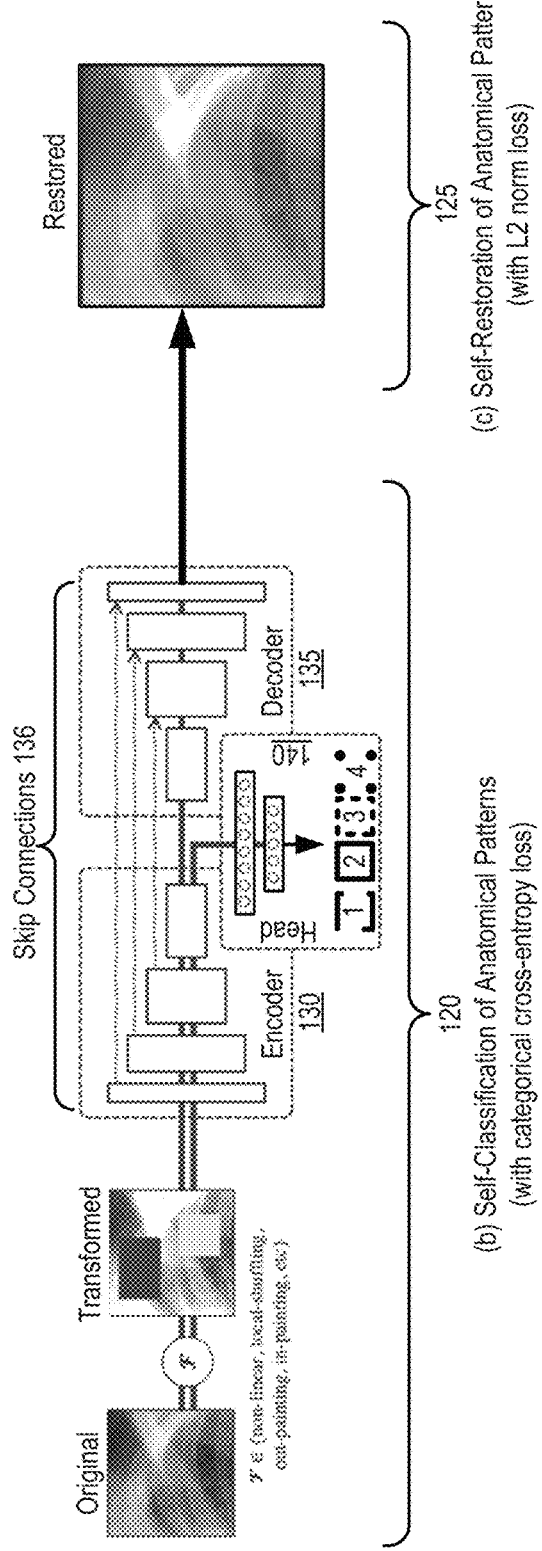

FIGS. 7A and 7B show how Semantic Genesis is dramatically different from Models Genesis and other prior known solutions in both methodology and performance.

Semantic Genesis, as disclosed herein, represents a significant advancement over prior known techniques such as Models Genesis, which heretofore was regarded as the state-of-the-art solution for a self-supervised learning framework for 3D medical transfer learning. Semantic Genesis attains such a feat because prior solutions are confined to only one capability, such as (c) self-restoration (similar that which is depicted at FIG. 7B, element 125), but without any additional capabilities whatsoever. To be clear, it was not simply that prior solutions chose not to utilize additional capabilities, but rather, prior known techniques were incompatible and unable to be successfully integrated with additional capabilities, and thus, had no mechanism whatsoever by which to additionally perform (a) self-discovery as depicted at FIG. 7A, element 115 and (b) self-classification as depicted at FIG. 7B, element 120.

It is these two new capabilities that enable Semantic Genesis to learn deep semantic representation from anatomical patterns, which are generated from the similar patients automatically determined in the deep latent space 799 (additional visualizations are provided at FIGS. 13A, 13B, 13C, and 13D). Furthermore, the ablation studies, presented in the lower portion of FIG. 7B at Table 5, confirm the importance of the capabilities (a) self-discovery 115 and (b) self-classification 120 because it is the semantics-enriched representation that leads to a significant performance improvement (p<0:05) for 2 out of 3 distinct medical applications. For the sake of simplicity and clarity, the concept is illustrated via 2D X-ray images, however, the Semantic Genesis is also trained using 3D CT sub-volumes with the same self-supervised learning framework according to the described embodiments.

FIGS. 8, 9, 10, and 11 depict the application of various transformations, as applied by Models Genesis, in accordance with described embodiments.

Visualizing transformed anatomical patterns: By leveraging the use of self-restoration of anatomical patterns (as described above), the disclosed model thus aims to learn general-purpose visual representation by recovering original anatomical patterns from their transformed corresponding variants. To automatically generate transformed anatomical patterns from X-ray images and CT scans, four image transformations techniques are disclosed and utilized in various combinations. All four transformations are reviewed and visualized, as follows: non-linear transformations 801 as set forth at FIG. 8, local-shuffling transformations 901 as set forth at FIG. 9, out-painting transformations 1001 as set forth at FIG. 10, and in-painting transformations 1101 as set forth at FIG. 11.

Figure 8:
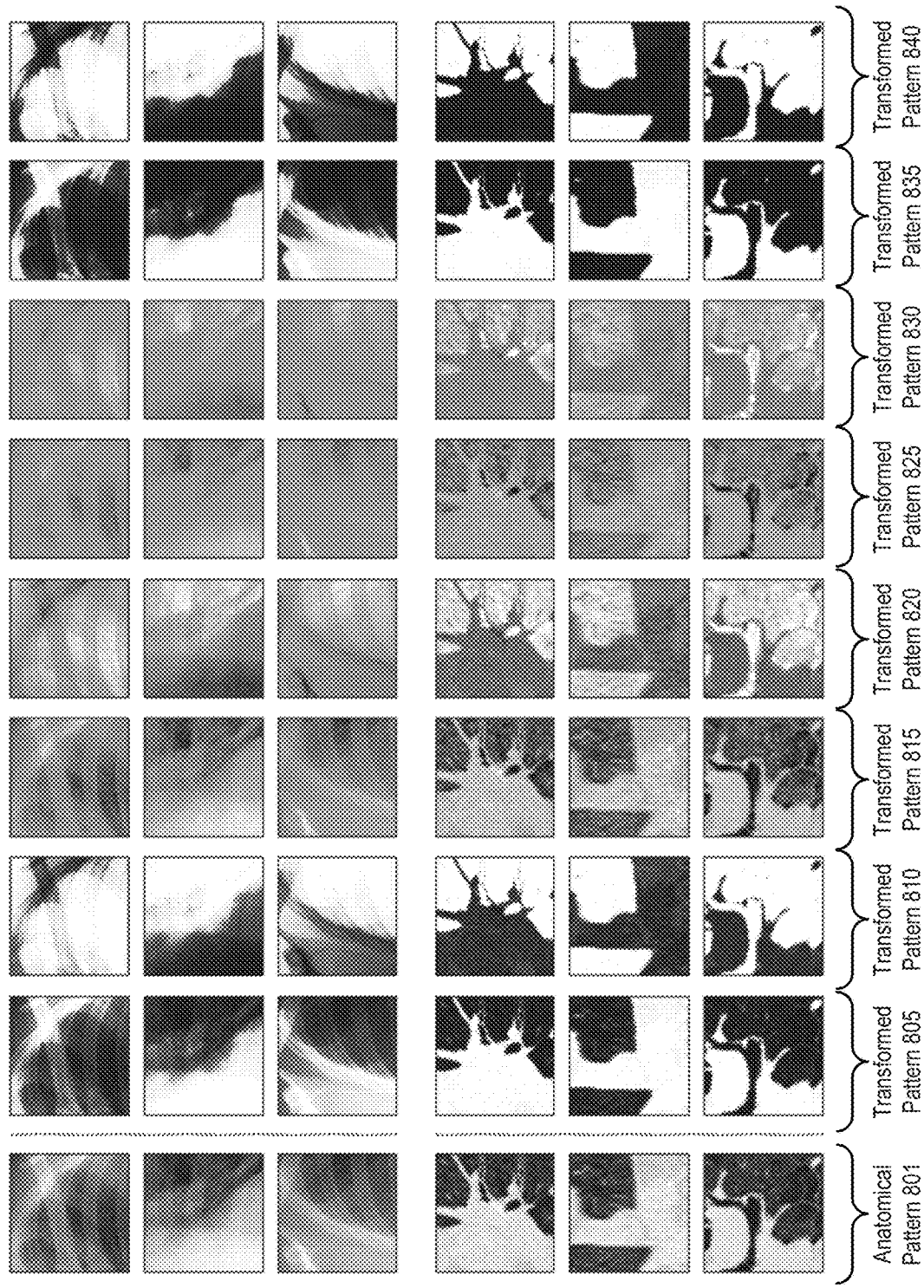
FIGS. 8, 9, 10, and 11 depict the application of various transformations, as applied by Models Genesis, in accordance with described embodiments.

With reference to FIG. 8, in Semantic Genesis, non-linear transformation available in Models Genesis is adopted as a self-restoration training scheme, from which the model learns to restore the intensity values of the input image transformed with a set of non-linear functions. Absolute or relative intensity values in medical images carry important information about anatomical structures and patterns. By restoring the original intensity values, the training scheme enables the model to learn the intensity distribution present in the medical images. In order to preserve relative intensity information of anatomies during image transformation, a monotonic transformation function is used to ensure that every pixel of different values is assigned with a unique value. Specifically, in prior techniques, such as Models Genesis, a Bézier Curve is implemented as the non-linear transformation function, which is generated from two end points ($P_0$ and $P_3$) and two control points ($P_1$ and $P_2$), defined as: $B(t)=(1-t)^3 P_0+3(1-t)^2 t P_1+3(1-t)t^2 P_2+t^3 P_3$, $t \in [0, 1]$, where t is a fractional value along the length of the line. By randomly generating two control points, it is theoretically possible to create an infinite number of transformed images. FIG. 8 thus illustrates both an original anatomical pattern 801 (shown via the left-most column) as well as eight examples of the transformed patterns of 2D CT and X-rays based on the non-linear transformation functions (shown via the second column from the left through to the right-most column, identified as transformed patterns 805, 810, 815, 820, 825, 830, 835, and 840). Notably, the original Models Genesis does not provide identifiable anatomical patterns, but rather, simply provides random patches. With respect to the disclosed methodologies, it is these semantics associated with anatomical patterns embedded in medical images that specifically enriches the representation learning thus and boosts the performance resulting in the superior performance when compared with previously known techniques.

Figure 9:
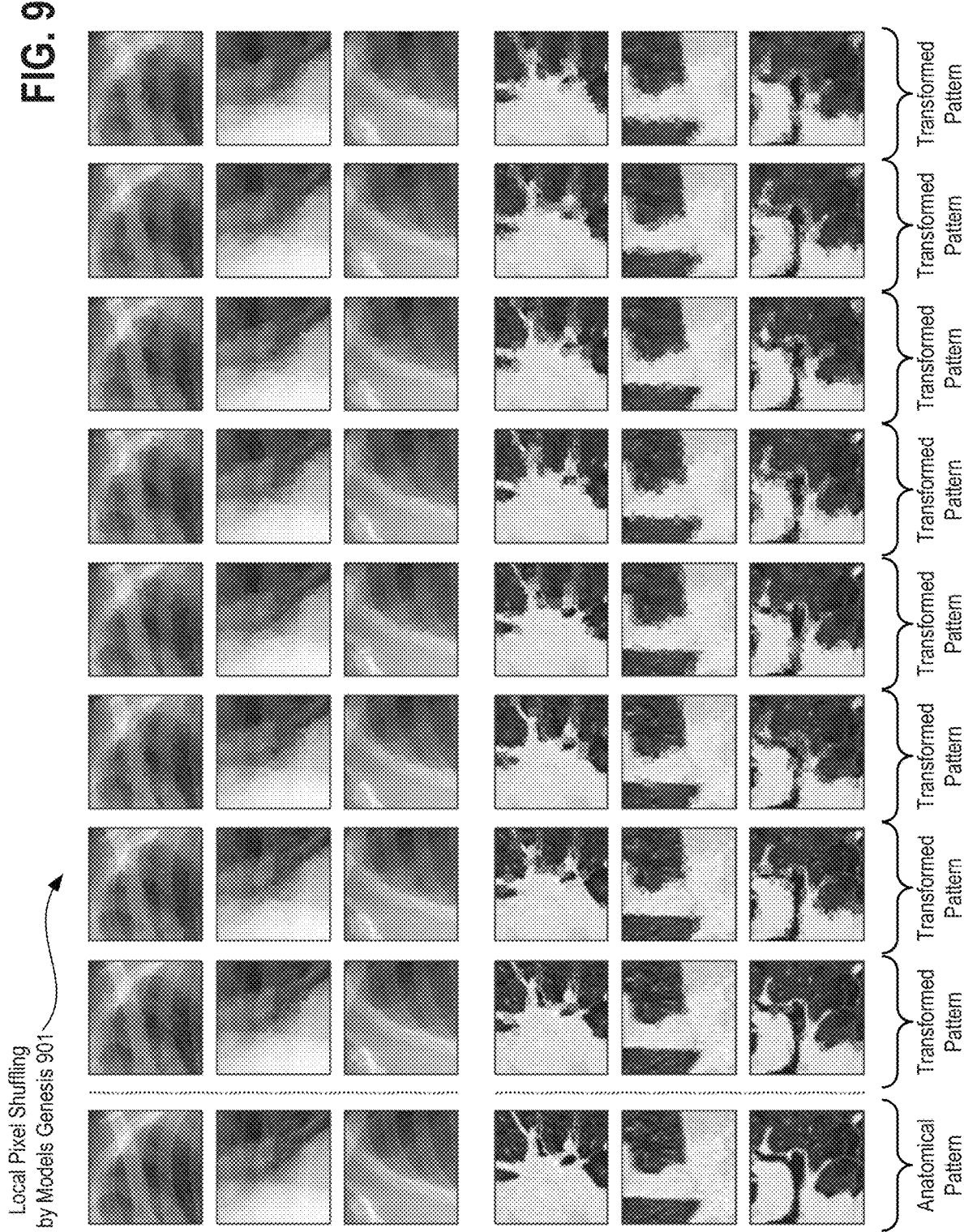

With reference to FIG. 9, in Semantic Genesis, local pixel shuffling available in Models Genesis is adopted as a self-restoration training scheme to encourage the model to learn the shapes and boundaries of the objects as well as the relative layout of different parts of the objects. To be specific, given an anatomical pattern, 1,000 windows from the pattern are randomly selected and then the pixels inside each window are sequentially shuffled. Mathematically, considering a small window W with the size of m×n, the local-shuffling acts on each window and can be formulated as $\tilde{W}=P \times W \times P'$, where $\tilde{W}$ is the transformed window, P and where P' denotes permutation metrics with the size of m×m and n×n, respectively. Pre-multiplying W with P permutes the rows of the window W, whereas post-multiplying W with P' results in the permutation of the columns of the window W. In practice, the window sizes are set smaller than the receptive field of the network so that the network can learn a more powerful visual representation by "resetting" the original pixel positions. For ease of understanding, presented at FIG. 9 are eight examples used in Semantic Genesis that have been transformed with local pixel shuffling and then visualized along with their original anatomical pattern (as shown at the left-most column). As shown here, local-shuffling within an extent maintains the objects perceivable, such that it will facilitate the deep neural network to learn invariant visual representations by restoring the original anatomical patterns. Again, in the prior known models, there simply is no concept of anatomical patterns but just random patches, and it is the semantics associated with anatomical patterns embedded in medical images that enriches the representation learning and enhances the performance.

Figure 10:
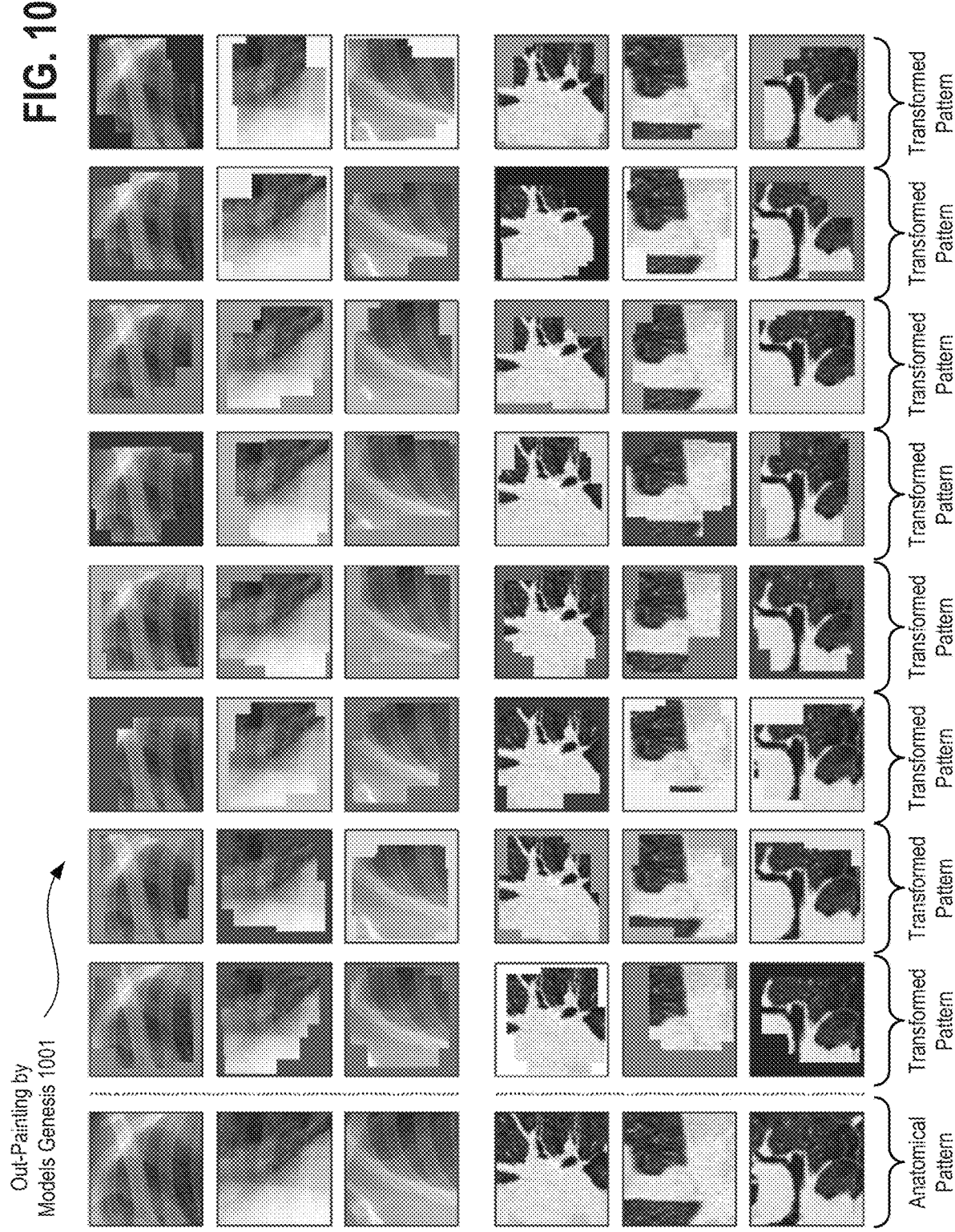

With reference to FIG. 10, in Semantic Genesis, out-painting available in Models Genesis is adopted as a self-restoration training scheme which allows the network to learn global geometry and spatial layout of organs in medical images by extrapolation. In known techniques, such as Models Genesis, an arbitrary number (≤10) of windows with various sizes and aspect ratios are generated and superimposed on top of each other, resulting in a single window of a complex shape. Ultimately, the pattern region inside the window is exposed and its surroundings are masked with a random number. Here, eight transformed anatomical patterns are illustrated utilizing the out-painting procedure and depicted in their transformed state along with their corresponding original pattern variant, as shown at the left-most column. Notably, so as to prevent the task from being too difficult or even unsolvable, the masked surrounding region is limited in accordance with certain embodiments so as to be smaller than ¼ of the entire pattern.

Figure 11:
Figure 13A:
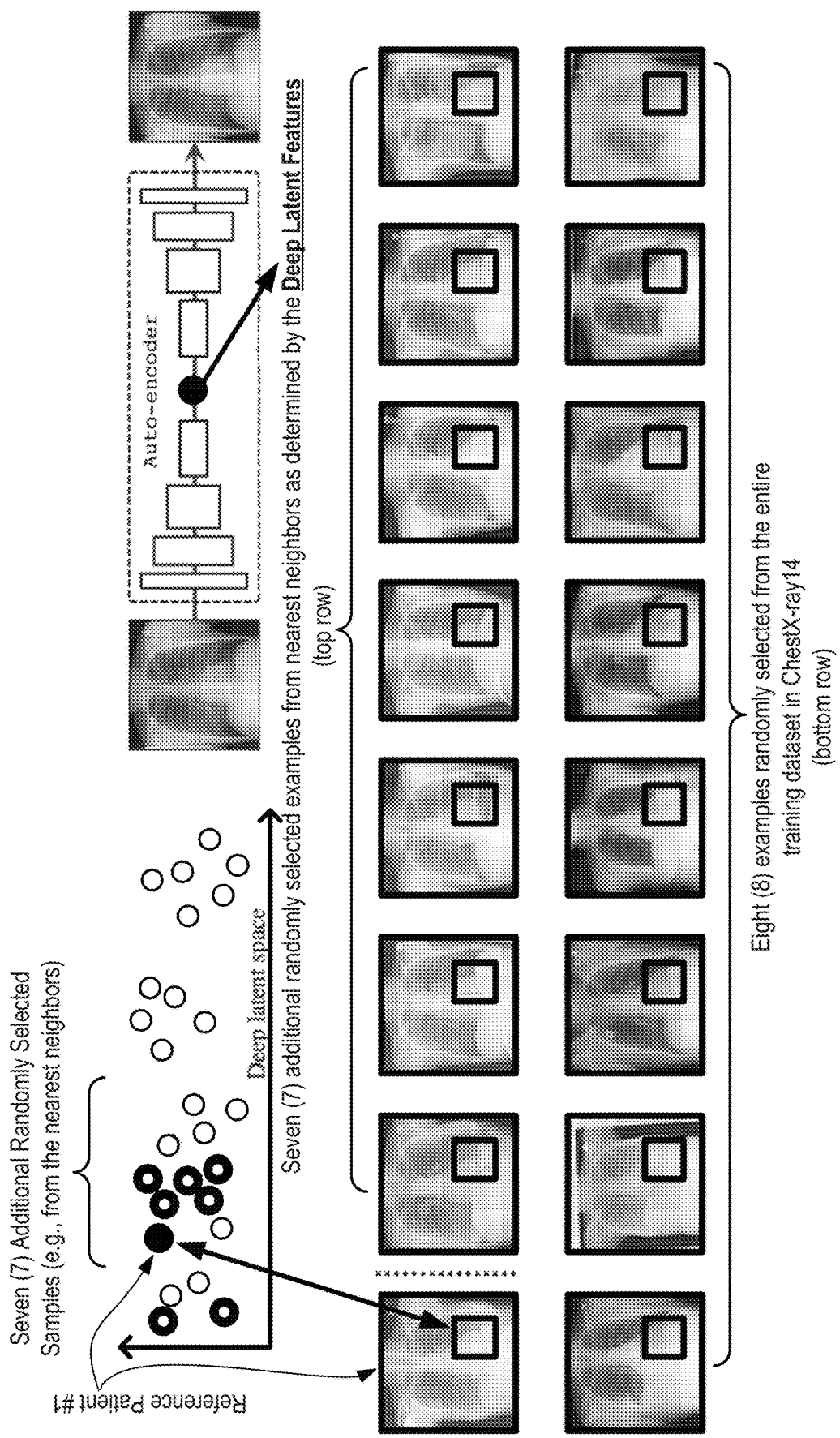
FIGS. 13A, 13B, 13C, 13D, 13E, and 13F provide additional exemplary reference samples for visualizing the self-discovery process in Semantic Genesis, in accordance with practice of the disclosed embodiments.
Figure 13B:
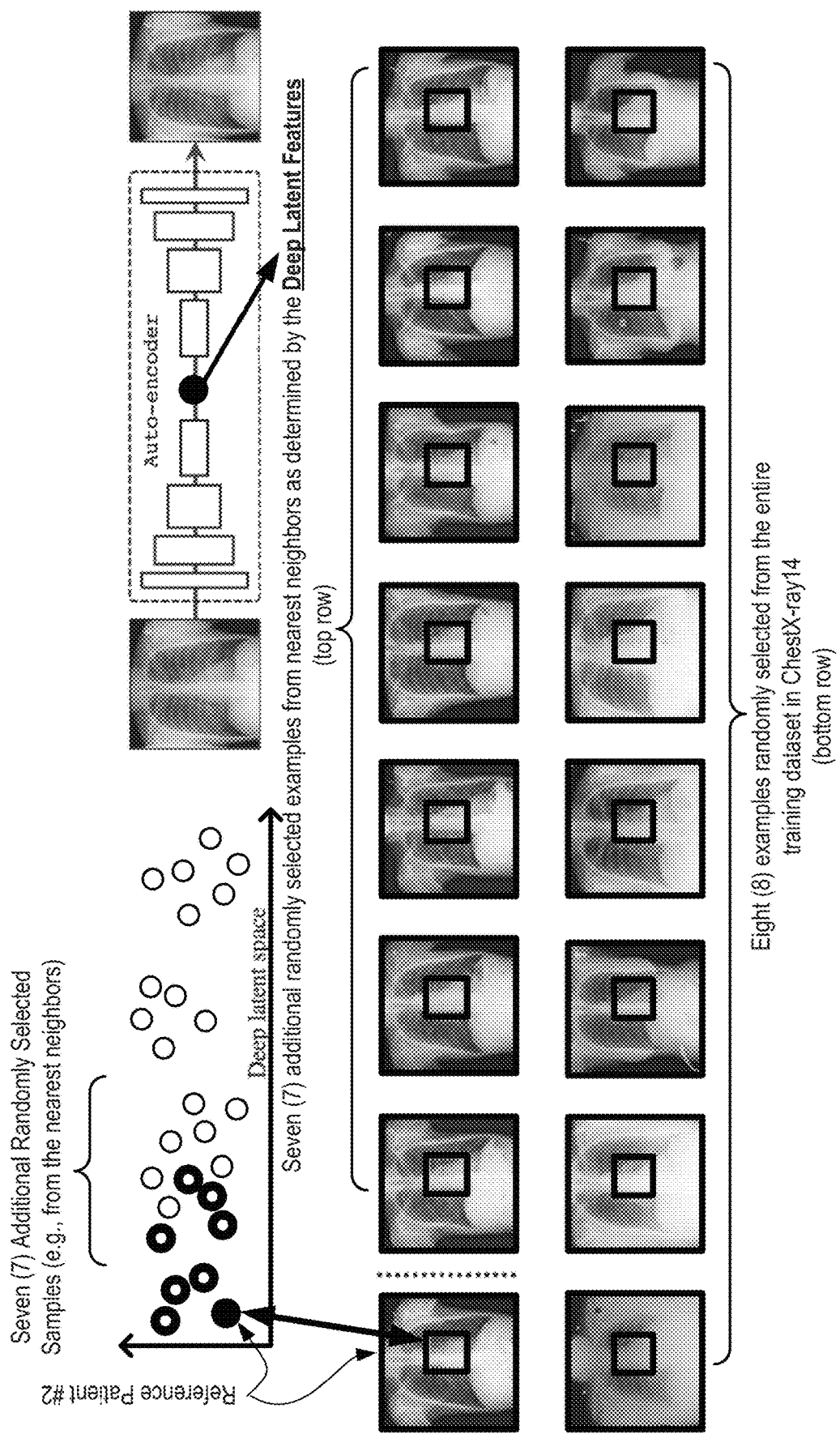
Figure 13C:
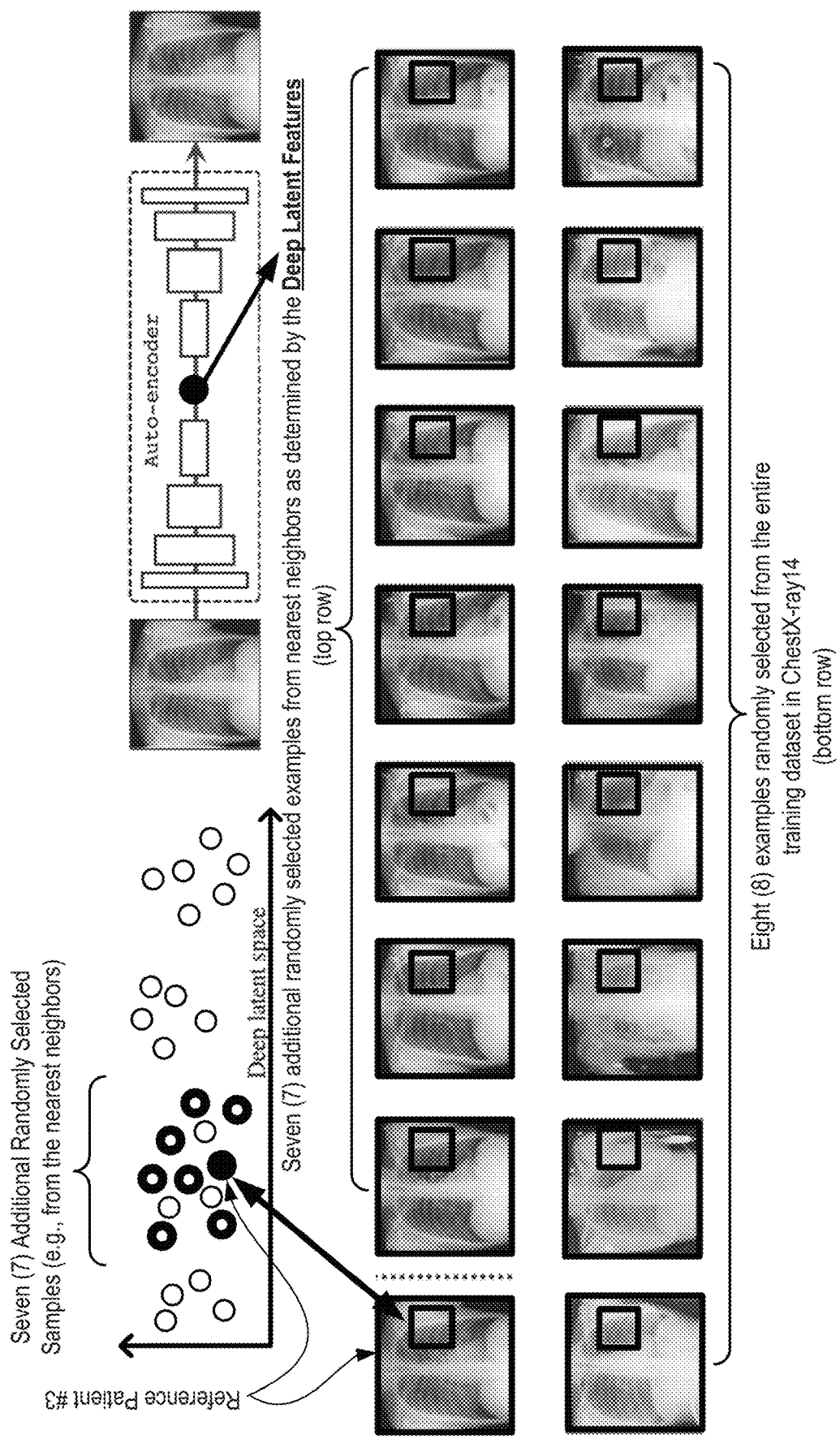
Figure 13D:
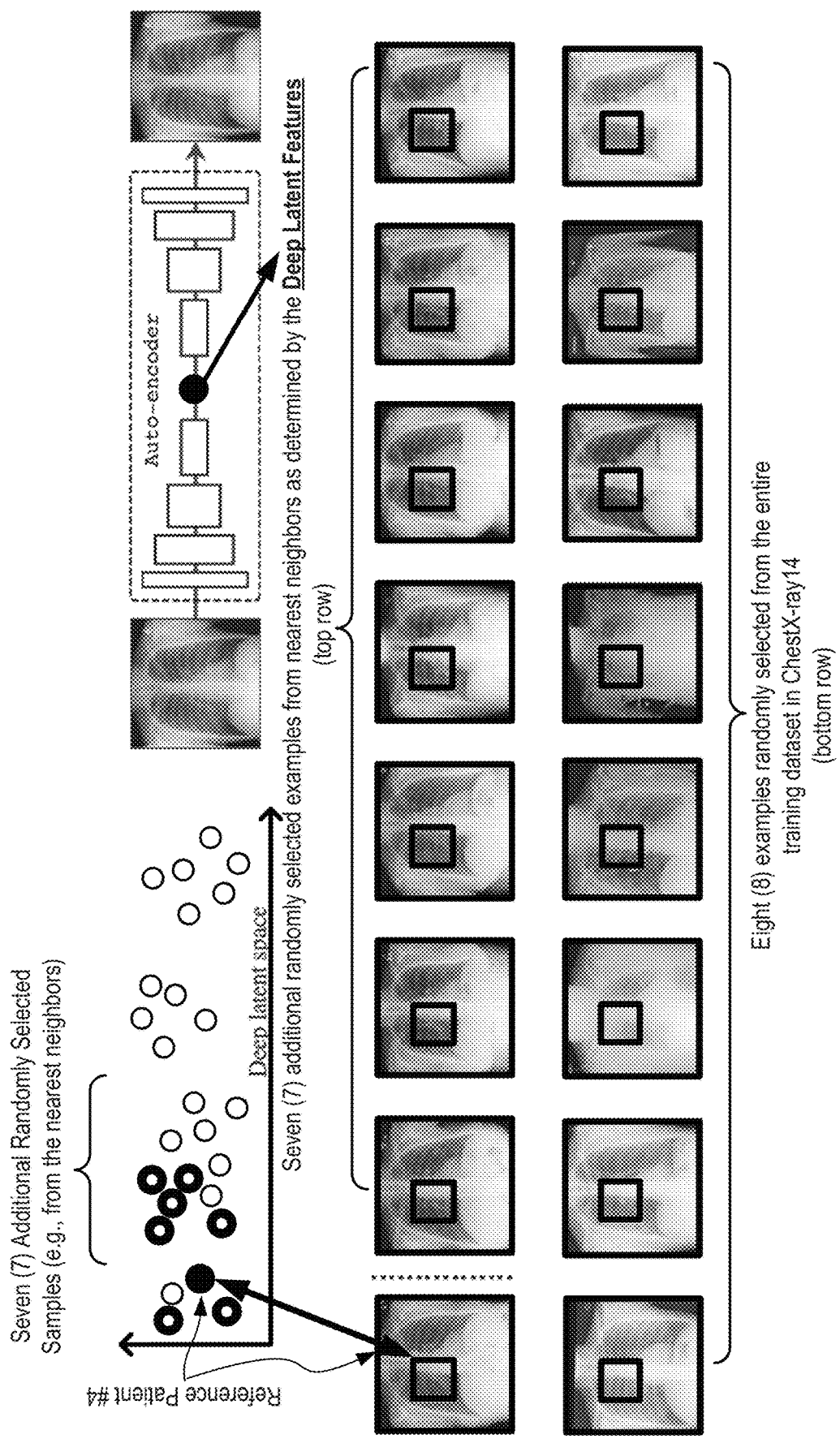
Figure 13E:
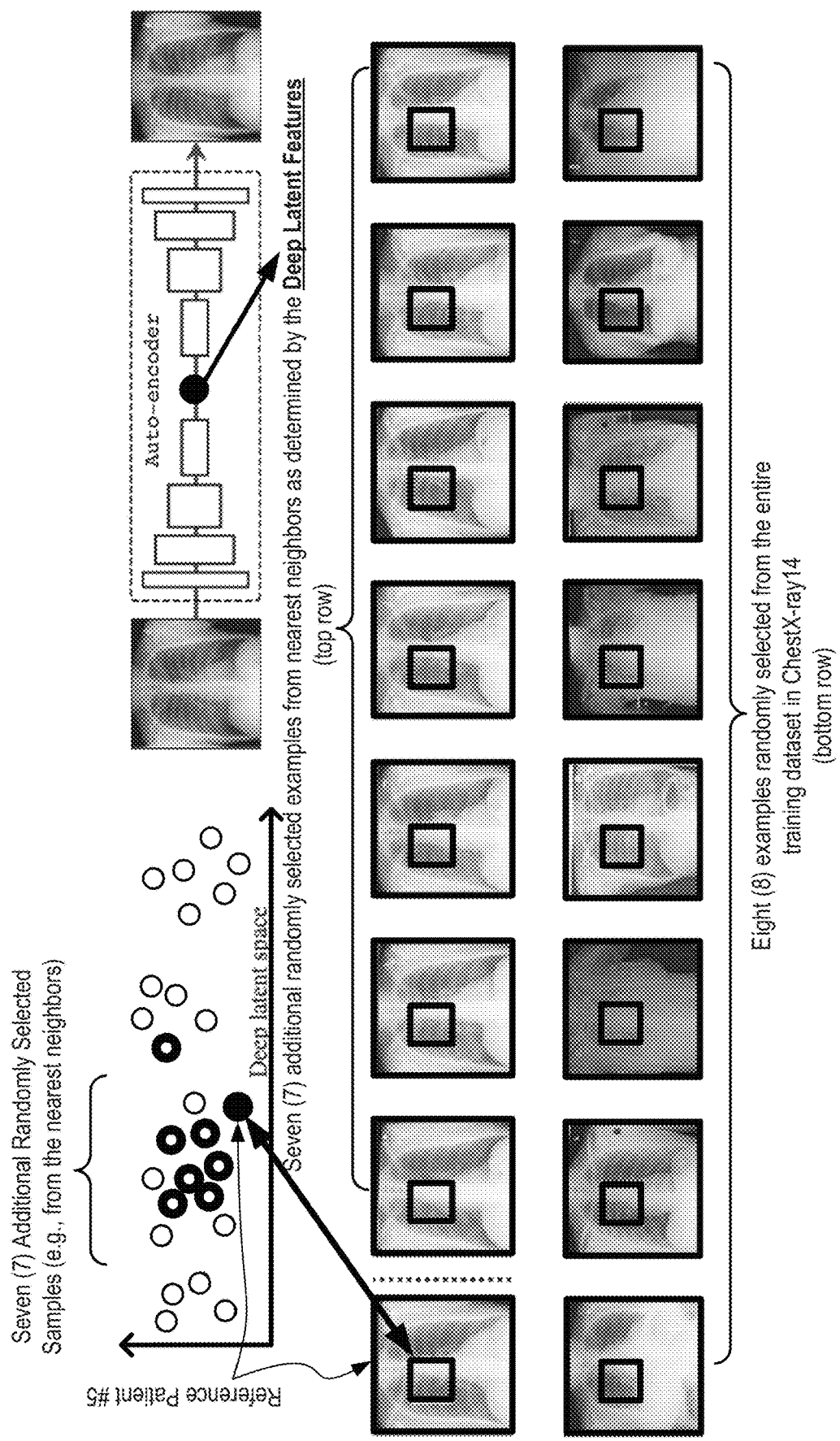
Figure 13F:
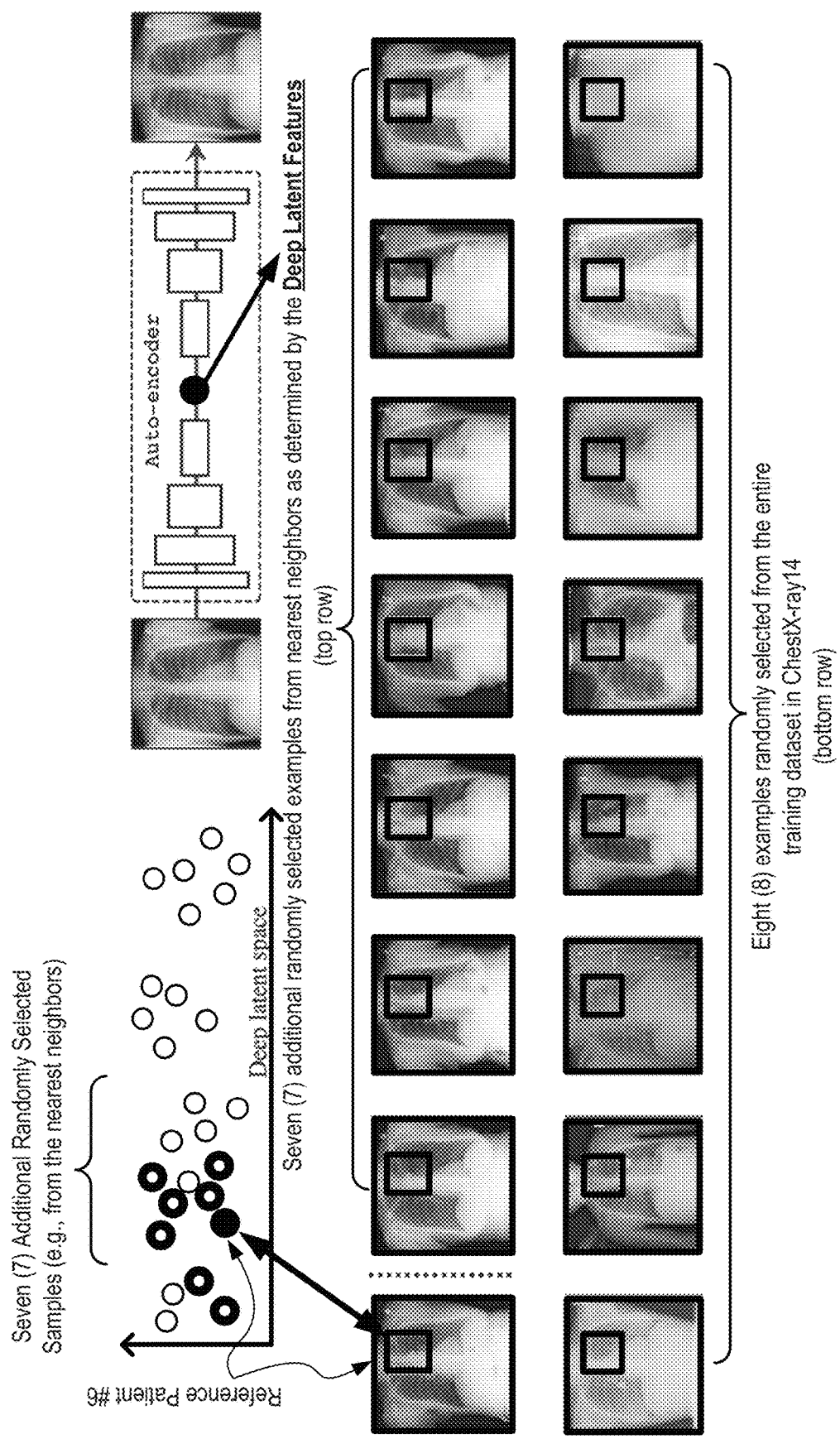

With reference to FIG. 11, in Semantic Genesis, in-painting available in Models Genesis is adopted as a self-restoration training scheme which allows the model to learn local shape and texture of organs in medical images via interpolation. According to such embodiments, the final transformed anatomical patterns are obtained by iteratively superimposing a window of random size and aspect ratio, filled with a random number, to the original pattern (as shown via the left-most column). Similar to out-painting, the masked areas for in-painting are also limited to be smaller than ¼ of the entire pattern in accordance with certain embodiments, so as to ensure the task is reasonably difficult but not impossible or unacceptably computationally burdensome.

FIG. 12 provides Table 6 at element 1295, which compares Semantic Genesis with publicly available pre-trained 3D models.

Specifically, Semantic Genesis is compared against three publicly available 3D pre-trained models, i.e. NiftyNet, Medical-Net, and Models Genesis. Notably, Semantic Genesis is pre-trained via self-supervision, without using any human annotation whatsoever, including forgoing the use of any human annotation which is shipped with the datasets, whereas both NiftyNet and MedicalNet are both explicitly pre-trained utilizing such human annotations via full supervision. Specifically, NiftyNet was adopted for the sake of such a comparison as it was pre-trained by segmenting multiple organs from abdominal CT. Most recently, MedicalNet has been released for 3D transfer learning, which is supervised co-trained on eight different 3D medical segmentation datasets by segmenting the objects annotated in the dataset and so it too was selected for comparison. Finally, Models Genesis have been regarded as the state-of-the-art self-supervised learning framework in 3D transfer learning, and thus is also utilized for comparison. Semantic Genesis was examined with these three highly competitive counterparts in two different medical target tasks, across diseases and organs, demonstrating that fine-tuning the Semantic Genesis as disclosed herein mostly yields significantly higher performances ($p<0.05$) when compared with NiftyNet, MedicalNet, and Models Genesis, while offering performance equivalent to Models Genesis in the nodule segmentation target task.

FIGS. 13A, 13B, 13C, 13D, 13E, and 13F provide additional exemplary reference samples for visualizing the self-discovery process in Semantic Genesis, in accordance with practice of the disclosed embodiments.

The power of the self-supervised learning framework as described herein is largely attributed to the similar anatomies and the consistent recurring anatomical patterns, which can be automatically discovered from medical images. To build a more comprehensive understanding of the proposed self-discovery learning scheme, six (6) reference patients are randomly anchored as the reference selected reference samples and then visualized through the self-discovery process as set forth at FIGS. 13A, 13B, 13C, 13D, 13E, and 13F corresponding to the randomly selected reference patients 1, 2, 3, 4, 5, and 6, respectively.

For each anatomical pattern, patches were extracted at the same coordinate across each of the respective patients and then grouped into one single class. That is to say, it is assumed that patches which are extracted at the same coordinate across images share a similar anatomical pattern. Nevertheless, randomly selecting patients from the ChestX-ray14 dataset (top row of each series of images at FIGS. 13A, 13B, 13C, 13D, 13E, and 13F) in practice fail to hold this assumption. It is because the patients appear differently from the reference and from each other, resulting in very different patterns when cropping at the same coordinate, as revealed in the in-set boxes within the upper series of images for each of the exemplary figures.

Therefore, similarity is first computed at the patient level using the deep latent features extracted from a pre-trained auto-encoder and then select the top nearest neighbors resulting in the series of images positioned at the lower row of each of FIGS. 13A, 13B, 13C, 13D, 13E, and 13F, representing each of the six reference patients. By cropping anatomical patterns from these similar patients (e.g., comparing the top row against the bottom row at each of the figures and not across figures), it is thus possible to strike a balance between consistency and diversity in pattern appearance for each anatomical pattern.

While the subject matter disclosed herein has been described by way of example and in terms of the specific embodiments, it is to be understood that the claimed embodiments are not limited to the explicitly enumerated embodiments disclosed. To the contrary, the disclosure is intended to cover various modifications and similar arrangements as are apparent to those skilled in the art. Therefore, the scope of the appended claims is to be accorded the broadest interpretation so as to encompass all such modifications and similar arrangements. It is to be understood that the above description is intended to be illustrative, and not restrictive. Many other embodiments will be apparent to those of skill in the art upon reading and understanding the above description. The scope of the disclosed subject matter is therefore to be determined in reference to the appended claims, along with the full scope of equivalents to which such claims are entitled.

What is claimed is:

1. A method performed by a system having at least a processor and a memory therein to execute instructions, wherein the method comprises:
    performing a self-discovery operation of anatomical patterns by (i) extracting deep features from each of a plurality of patient scans within a dataset, (ii) training an auto-encoder network utilizing training data, and (iii) selecting a random patient scan from the dataset as a reference image and identifying a set of semantically similar patients to the reference image within the dataset;
    performing a self-classification operation of anatomical patterns by encoding input anatomical patterns into a latent space, followed by a sequence of fully-connected (fc) layers to predict a pseudo label associated with each pattern, wherein the anatomical patterns are classified via a categorical cross-entropy loss function; and
    performing a self-restoration operation of anatomical patterns by (i) transforming the input anatomical patterns forming transformed anatomical patterns, (ii) encoding the transformed anatomical patterns into a latent space, and (iii) decoding the transformed anatomical patterns to recover the original input anatomical patterns from the transformed anatomical patterns forming reconstructed anatomical patterns.

2. The method of claim 1, wherein simultaneous processing executes both the self-classification operation and the self-restoration operation in parallel.

3. The method of claim 2, further comprising:
    training a Semantic Genesis model by having the Semantic Genesis model simultaneously classify and restore the transformed anatomical patterns.

4. The method of claim 1, wherein performing the method works with both 2D and 3D input images.

5. The method of claim 1, further comprising:
    computing an L2 distance between the original input anatomical patterns and the reconstructed anatomical patterns as a loss function.

6. The method of claim 1, wherein transforming the input anatomical patterns forming transformed anatomical patterns comprises applying one or more transformation functions selected from the group comprising:
    (i) a non-linear transformation function,
    (ii) a local-shuffling transformation function,
    (iii) an out-painting transformation function, and
    (iv) an in-painting transformation function.

7. The method of claim 1, wherein the patient scans within the dataset are not manually annotated.

8. Non-transitory computer-readable storage media having instructions stored thereupon that, when executed by a system having at least a processor and a memory therein, the instructions cause the system to perform operations including:

performing a self-discovery operation of anatomical patterns by (i) extracting deep features from each of a plurality of patient scans within a dataset, (ii) training an auto-encoder network utilizing training data, and (iii) selecting a random patient scan from the dataset as a reference image and identifying a set of semantically similar patients to the reference image within the dataset;

performing a self-classification operation of anatomical patterns by encoding input anatomical patterns into a latent space, followed by a sequence of fully-connected (fc) layers to predict a pseudo label associated with each pattern, wherein the anatomical patterns are classified via a categorical cross-entropy loss function; and performing a self-restoration operation of anatomical patterns by (i) transforming the input anatomical patterns forming transformed anatomical patterns, (ii) encoding the transformed anatomical patterns into a latent space, and (iii) decoding the transformed anatomical patterns to recover the original input anatomical patterns from the transformed anatomical patterns forming reconstructed anatomical patterns.

9. The non-transitory computer readable storage media of claim 8, wherein simultaneous processing executes both the self-classification operation and the self-restoration operation in parallel.

10. The non-transitory computer readable storage media of claim 9, wherein the instructions, when executed by the processor of the system, the instructions cause the system to perform further operations comprising:

training a Semantic Genesis model by having the Semantic Genesis model simultaneously classify and restore the transformed anatomical patterns.

11. The non-transitory computer readable storage media of claim 8, wherein performing the method works with both 2D and 3D input images.

12. The non-transitory computer readable storage media of claim 8, wherein the instructions, when executed by the processor of the system, the instructions cause the system to perform further operations comprising:

computing an L2 distance between the original input anatomical patterns and the reconstructed anatomical patterns as a loss function.

13. The non-transitory computer readable storage media of claim 8, wherein transforming the input anatomical patterns forming transformed anatomical patterns comprises applying one or more transformation functions selected from the group comprising:

(i) a non-linear transformation function,
(ii) a local-shuffling transformation function,
(iii) an out-painting transformation function, and
(iv) an in-painting transformation function.

14. The non-transitory computer readable storage media of claim 8, wherein the patient scans within the dataset are not manually annotated.

15. A system comprising:
a memory to store instructions;
a processor to execute the instructions stored in the memory;
wherein the system is specially configured to:
execute instructions via the processor for performing a self-discovery operation of anatomical patterns by (i) extracting deep features from each of a plurality of patient scans within a dataset, (ii) training an auto-encoder network utilizing training data, and (iii) selecting a random patient scan from the dataset as a reference image and identifying a set of semantically similar patients to the reference image within the dataset;
execute instructions via the processor for performing a self-classification operation of anatomical patterns by encoding input anatomical patterns into a latent space, followed by a sequence of fully-connected (fc) layers to predict a pseudo label associated with each pattern, wherein the anatomical patterns are classified via a categorical cross-entropy loss function; and
execute instructions via the processor for performing a self-restoration operation of anatomical patterns by (i) transforming the input anatomical patterns forming transformed anatomical patterns, (ii) encoding the transformed anatomical patterns into a latent space, and (iii) decoding the transformed anatomical patterns to recover the original input anatomical patterns from the transformed anatomical patterns forming reconstructed anatomical patterns.

16. The system of claim 15, wherein simultaneous processing executes both the self-classification operation and the self-restoration operation in parallel; and
wherein the system is further specially configured to execute instructions via the processor for training a Semantic Genesis model by having the Semantic Genesis model simultaneously classify and restore the transformed anatomical patterns.

17. The system of claim 15, wherein performing the method works with both 2D and 3D input images.

18. The system of claim 15, wherein the system is further specially configured to:
execute instructions via the processor for computing an L2 distance between the original input anatomical patterns and the reconstructed anatomical patterns as a loss function.

19. The system of claim 15, wherein transforming the input anatomical patterns forming transformed anatomical patterns comprises applying one or more transformation functions selected from the group comprising:
(i) a non-linear transformation function,
(ii) a local-shuffling transformation function,
(iii) an out-painting transformation function, and
(iv) an in-painting transformation function.

20. The system of claim 15, wherein the patient scans within the dataset are not manually annotated.

* * * * *